United States Patent
Jang et al.

(10) Patent No.: US 12,158,426 B2
(45) Date of Patent: Dec. 3, 2024

(54) RAMAN OPTICAL BIOMARKER FOR SHADE AVOIDANCE SYNDROME IN PLANTS

(71) Applicants: TEMASEK LIFE SCIENCES LABORATORY LIMITED, Singapore (SG); MASSACHUSETTS INSTITUTE OF TECHNOLOGY, Cambridge, MA (US)

(72) Inventors: In-Cheol Jang, Singapore (SG); Benny Jian Rong Sng, Singapore (SG); Gajendra Pratap Singh, Singapore (SG); Rajeev J. Ram, Cambridge, MA (US)

(73) Assignees: TEMASEK LIFE SCIENCES LABORATORY LIMITED, Singapore (SG); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 216 days.

(21) Appl. No.: 17/999,331

(22) PCT Filed: May 20, 2021

(86) PCT No.: PCT/SG2021/050275
§ 371 (c)(1),
(2) Date: Nov. 18, 2022

(87) PCT Pub. No.: WO2021/236014
PCT Pub. Date: Nov. 25, 2021

(65) Prior Publication Data
US 2023/0243750 A1    Aug. 3, 2023

(30) Foreign Application Priority Data
May 21, 2020    (SG) .......................... 10202004761W

(51) Int. Cl.
*G01N 21/65* (2006.01)
*G01N 21/84* (2006.01)
*G01N 33/00* (2006.01)

(52) U.S. Cl.
CPC ............. *G01N 21/65* (2013.01); *G01N 21/84* (2013.01); *G01N 33/0098* (2013.01); *G01N 2021/8466* (2013.01)

(58) Field of Classification Search
CPC ....... G01N 33/0098; G01N 2021/8466; G01N 21/65; G01J 4/04
See application file for complete search history.

(56) References Cited

U.S. PATENT DOCUMENTS
2005/0282229 A1    12/2005  Su et al.
2016/0335477 A1    11/2016  Young et al.

FOREIGN PATENT DOCUMENTS
CN     108007916 A      5/2018
WO     WO-0078217 A1 * 12/2000    ......... A61B 5/14546
WO     WO-02077608 A2 * 10/2002   ................ G01J 3/44

OTHER PUBLICATIONS

Vanessa E. de Oliveira, "Carotenes and carotenoids in natural biological samples: a Raman spectroscopic analysis", Aug. 18, 2009 (Year: 2009).*

(Continued)

*Primary Examiner* — Maurice C Smith
(74) *Attorney, Agent, or Firm* — Rothwell, Figg, Ernst and Manbeck, P.C.

(57) ABSTRACT

The present invention relates to the use of a Raman spectral signature for detection of plant metabolites, specifically carotenoids, in tissue of a plant leaf. Carotenoids are used as a biomarker for an early, real-time diagnosis of shade avoidance syndrome (SAS) in growing plants in a non-invasive or non-destructive way in order to detect the adverse effect of the SAS upon their health, and ultimately (Continued)

their yield. The early, real-time diagnosis of SAS provides a window period within which further adverse effects of SAS may be slowed or prevented without negatively affecting the yield of growing plants or leafy vegetables.

10 Claims, 18 Drawing Sheets

Specification includes a Sequence Listing.

(56) References Cited

OTHER PUBLICATIONS

E. Schäfer and F. Nagy (eds.), Photomorphogenesis in Plants and Bacteria, 3rd ed., 475-497. © 2006 Springer (Year: 2006).*
Cai, X. et al., "Effects of shading on leaf morphology, photosynthetic characteristics, and growth of lex asprella", Journal of Tropical and Subtropical Botany, Feb. 29, 2020, vol. 28, No. 1, pp. 25-34.
Zou, C.M. et al., "Response of photosynthesis and growth to weak light regime in four legume species", Chin J of Plan Ecology, Dec. 31, 2015, vol. 39, No. 9, pp. 909-916.
Sebastiani, F. et al., "Dissecting Adaptation Mechanisms to Contrasting Solar Irradiance in the Mediterranean Shrub Cistus incanus", Int J Mol Sci, Jul. 23, 2019, vol. 20, No. 14, Article 3599 (pp. 1-20).
Fan, Y. et al., "Effect of shading and light recovery on the growth, leaf structure, and photosynthetic performance of soybean in a maize-soybean relay-strip intercropping system", PLoS One, May 31, 2018, vol. 13, No. 5, Article e0198159 (pp. 1-15).
Panigrahy, M. et al., "Shade tolerance in Swarnaprabha rice is associated with higher rate of panicle emergence and positively regulated by genes of ethylene and cytokinin pathway", Sci Rep, May 2, 2019, vol. 9, No. 1, Article 6817 (pp. 1-17).
Schulz H. et al., "Potential of NIR-FT-Raman spectroscopy in natural carotenoid analysis", Biopolymers, Mar. 31, 2005, vol. 77, No. 4, pp. 212-221.
Sng, B.J.R. et al., "Rapid metabolite response in leaf blade and petiole as a marker for shade avoidance syndrome", Plant Methods, Oct. 27, 2020, vol. 16, Article 144 (pp. 1-17).
International Search Report issued in PCT/SG2021/050275 dated Jul. 14, 2021, 3 pages.
Butler, H.J. et al., "Observation of nutrient uptake at the adaxial surface of leaves of tomato (Solanum lycopersicum) using Raman spectroscopy", Analytical Letters, Sep. 4, 2019, vol. 53, No. 4, pp. 536-562.
Butler, H.J. et al., "Application of vibrational spectroscopy techniques to non-destructively monitor plant health and development", Analytical Methods, Apr. 2, 2015, vol. 7, No. 10, pp. 4059-4070.
Huang, C. H. et al., "Early Diagnosis and Management of Nitrogen Deficiency in Plants Utilizing Raman Spectroscopy", Frontiers in Plant Science, Jun. 5, 2020, vol. 11, Article 663, pp. 1-13.
Gupta, S. et al., "Portable Raman leaf-clip sensor for rapid detection of plant stress", Scientific reports, Nov. 19, 2020, vol. 10, No. 20206, pp. 1-10.
Lew, T.T.S. et al., "Species-independent analytical tools for next-generation agriculture", Nature Plants, Dec. 2020, vol. 6, pp. 1408-1417.
International Search Report issued in PCT/SG2021/050276 dated Jul. 30, 2021, 5 pgs.

* cited by examiner

RAMAN OPTICAL BIOMARKER FOR SHADE AVOIDANCE SYNDROME IN PLANTS

CROSS-REFERENCE TO RELATED APPLICATIONS

This application is a 35 U.S.C. 371 National Phase Entry Application from PCT/SG2021/050275 filed May 20, 2021, which claims priority to and the benefit of Singapore patent application Ser. No. 10/202,004761W, filed on May 21, 2020, the disclosures of which are incorporated herein by reference in their entirety.

BACKGROUND OF THE INVENTION

The present invention relates to the use of Raman spectroscopy to identify a spectral biomarker that is associated with shade avoidance syndrome (SAS) in plants, which then can be used for the early, real-time diagnosis of SAS in plants and ultimately for preventing or slowing further development of SAS in plants.

The publications and other materials used herein to illuminate the background of the invention or provide additional details respecting the practice, are incorporated by reference, and for convenience are respectively grouped in the Bibliography.

Plants are sessile organisms that cannot escape from its environment even when it becomes unfavorable. As such, it is crucial for plants to sense its surroundings and mount appropriate responses to different stresses. In vegetative shade, poor light quantity (fluence) and quality (wavelength) affects photosynthesis and plant development (1). Specifically, vegetative shade has reduced Red:Far-red (R:FR) light ratio, which is sensed by phytochromes, a family of R/FR absorbing photoreceptors in plants (1,2). Upon exposure to vegetative shade, plants respond by reaching for more light to overcome the shaded condition. However, this weakens the plant's structure and immunity (1,2). This adaptive response, known as shade avoidance syndrome (SAS), includes stem and petiole elongation, hyponastic leaves, reduced leaf development, early flowering, and increased senescence (1,2). Hence, SAS affects many agronomic traits such as reduced grain yield or plant biomass (3,4).

Studies of SAS largely focused at the genetic level using the model plant *Arabidopsis thaliana*, as they characterized genes involved in the signaling mechanisms underlying SAS (5,6,7). While gene expression is important to understand the initial response of shade-avoiding plants, downstream changes to hormones and metabolites are also crucial in determining the plant's final morphological and physiological response (8,9).

Hormonal studies of SAS have become more comprehensive in recent years (8,9), but so far, few studies investigated the changes in metabolites under SAS (10,11). Current analytical techniques for plant hormones/metabolites have evolved with the advancement of chromatography and mass spectrometry (12,13). Although these conventional methods are specific and accurate, their analysis can also be complex, as they depend on the extraction method and metabolites of interest (14). Moreover, sample preparation is usually the limiting step in plant hormone/metabolite analysis. Therefore, there is a need for new technologies to easily monitor metabolite levels in a non-invasive manner and in real-time.

In the last decade, optical spectroscopies, in particular Raman spectroscopy, have been widely used for real-time measurements of metabolites in microbial and mammalian cells (15,16,17,18,19). Raman spectroscopy, discovered in 1928 by C. V. Raman and K. S. Krishnan (20), measures the inelastic scattering of laser light that results in a characteristic 'fingerprint' of vibrational frequencies for each molecular species present. The convergence of interest in plant metabolomics and maturity of Raman spectroscopy has stimulated recent exploration of optical biomarkers in plants. Altangerel et al. (21) describe the study of Raman spectra of carotenoids and anthocyanins in environmental stresses such as cold, high light, drought, and salinity. In another example, U.S. Pat. No. 7,215,420 B2 discloses use of Raman spectroscopy as a quality control measure to determine freshness of the harvested agricultural products such as fruits and vegetables, including leafy vegetables, their anti-oxidant levels for classifying the agricultural products as desirable or undesirable as a function of their carotenoid (amongst others) concentration level. WO2009149266 uses Raman spectroscopy to measure carotenoid in fruits and vegetables as a biomarker for fruit and vegetable intake.

Shade avoidance syndrome (SAS) commonly occurs in plants experiencing vegetative shade, causing morphological and physiological changes that are detrimental to plant health and consequently crop yield. However, conventional assessment of SAS is restricted to measuring morphology and checking the expression of shade-induced genes. It is desired to develop methods and systems that can be used to non-destructively and non-invasively measure changes of metabolites in vivo and to assess the severity of SAS in a shaded plant.

SUMMARY OF THE INVENTION

The present invention relates to the use of Raman spectroscopy to identify a spectral biomarker that is associated with shade avoidance syndrome (SAS) in plants, which then can be used for the early, real-time diagnosis of SAS in plants and ultimately for slowing or preventing further development of SAS in plants. More specifically, the present invention relates to the use of a Raman spectral signature of plant metabolites, specifically carotenoids, as a biomarker for an early, real-time diagnosis of SAS in growing plants in a non-invasive or non-destructive way in order to detect the adverse effect of the SAS upon their health, and ultimately their yield. The early, real-time diagnosis of SAS provides a window period within which further adverse effects of the SAS can be slowed or prevented without negatively affecting the yield of growing plants or leafy vegetables.

The invention uses Raman spectral signature of plant metabolites, specifically carotenoids, as a biomarker for an early, real-time diagnosis of SAS, a syndrome, caused by low red/far-red light and high-density conditions, in growing plants in a non-invasive or non-destructive way, wherein plants need not be "destroyed" in order to detect the adverse effect of the SAS upon their health, and ultimately the yield. Raman spectroscopy at near-infrared (830 nm) excitation wavelength accurately detects changes in concentration of carotenoids due to SAS by changes in intensity of Raman signals at 1004 $cm^{-1}$, 1150 $cm^{-1}$ and 1521 $cm^{-1}$. Changes in carotenoids are detected before and while morphological changes occurred, highlighting carotenoids as an indicator metabolite of SAS and Raman spectroscopy as a predictive tool for early diagnosis. Raman-based signatures can be used in a hand-held Raman spectroscope to detect the SAS in plants under shade stress. Any Raman spectroscope can be used in the invention for detecting SAS.

The early, real-time diagnosis of the SAS provides a window period within which further adverse effects of the SAS can be slowed or prevented without negatively affecting the yield of growing plants, or leafy vegetables. Plants affected by the SAS tend to grow long petioles and small leaf-blades thereby reducing the yield in leafy vegetables. Early diagnosis of SAS enables treating the SAS in time to prevent or slow further development of SAS, and to ensure yield of leafy vegetables growing in, particularly, artificial urban farming settings.

Thus, in one aspect, the present invention provides a method of diagnosing Shade Avoidance Syndrome (SAS) in a plant. In accordance with this aspect, the method comprises:

(a) obtaining a Raman spectra of carotenoids in vivo and in situ (i.e., in planta) in tissue of a plant leaf at a first point in time, wherein the Raman spectra includes one or more peaks characteristic of carotenoids;

(b) obtaining a Raman spectra of carotenoids in vivo and in situ in the tissue of the plant leaf at a second point in time, wherein the Raman spectra includes the one or more peaks characteristic of carotenoids;

(c) comparing intensity of the one or more peaks characteristic of carotenoids from the Raman spectra obtained at the first point of time with intensity of the one or more peaks characteristic of carotenoids from the Raman spectra obtained at the second point of time; and (d) determining if there is a decrease in the relative intensity of one or more peaks characteristic of carotenoids from the Raman spectra obtained at the second point in time, wherein a decrease in relative intensity of the one or more peaks characteristic of carotenoids from the Raman spectra obtained at the second point of time is indicative of SAS.

In some embodiments, the tissue of the plant leaf is a leaf blade or a leaf petiole. In other embodiments, the tissue of the plant leaf is the leaf blade. In some embodiments, the one or more peaks characteristic of carotenoids in the Raman spectra are selected from the group of peaks consisting of $1004\ cm^{-1}$, $1150\ cm^{-1}$ and $1521\ cm^{-1}$. In other embodiments, the Raman spectra is obtained using near-infrared excitation wavelength. In some embodiments, the near-infrared excitation wavelength is 830 nm. In other embodiments, obtaining the Raman spectra is non-invasive and non-destructive to the tissue of the plant leaf.

In another aspect, the present invention provides a method of preventing or slowing the further development of Shade Avoidance Syndrome (SAS) in a plant comprising: (a) diagnosing SAS in a plant according to a method described herein and (b) reducing the amount of shade affecting the plant. In some embodiments, shade is reduced by providing light to the plant. In other embodiments, shade is reduced by trimming nearby plants.

BRIEF DESCRIPTION OF THE FIGURES

FIG. 2a. Phenotype of 17 d old WT *Arabidopsis* plants under white light (WL) and two different shade conditions, moderate shade (MS) and deep shade (DS). Upper panel, top-down view of plant. Lower panel, side view of plant. Scale, 1 cm. FIG. 2b. Ratio of petiole length to leaf blade area for visualising severity of SAS (n=8). FIG. 2c. Relative expression of shade-induced genes in *Arabidopsis* plants in (FIG. 2a) (n=3). FIG. 2d. Total carotenoids content (µg/g fresh weight) of plants in (FIG. 2a) (n=3). FIG. 2e. Raman spectrum peaks representing carotenoids ($1004\ cm^{-1}$, $1150\ cm^{-1}$ and $1521\ cm^{-1}$) of *Arabidopsis* under shade conditions in (FIG. 2a) (leaf blade: n=8, petiole: n=4). FIG. 2f. Relative gene expression of carotenoids biosynthesis genes (DXS, DXR, HDR, PSY, and PDS) in *Arabidopsis* plants in (FIG. 2a) (n=3). Bars denote average±SE. Statistical significance between WL and shade was determined by Student's t-test: *, $P<0.05$; , $P<0.01$; *, $P<0.001$.

FIG. 3a. Measurements of petiole length and leaf blade area of wild type (Col-0) *Arabidopsis* plants grown in shade conditions. Bars denote average±SE (n=4). FIG. 3b. Left panel, Raman spectrum for each leaf number. Inset focused on $1521\ cm^{-1}$ Raman peak. Right panel, measured peak intensities at $1521\ cm^{-1}$ Raman shift. Bars denote average±SE (n=8). FIG. 3c. Development of leaf number 3 of *Arabidopsis* plant. Numbers represent leaf number, according to order of development. C represents cotyledon. Scale, 1 cm. WL, white light; MS, moderate shade; DS, deep shade; DAG, days after germination.

FIG. 4a. Raman spectra of *Arabidopsis* leaf blades and petioles under different shade conditions. (leaf blade: n=8, petiole: n=4). FIG. 4b. Three-dimensional principal component analysis (PCA) plot of wild type (Col-0) *Arabidopsis* under shade conditions. FIG. 4c. Raman spectra for carotenoid standards. WL, white light; MS, moderate shade; DS, deep shade FIG. 5a. Schematic diagram of different durations of shade treatment. WL, white light; DS, deep shade. FIG. 5b. Phenotype of plants under time-course shade treatment. 10 d-old *Arabidopsis* plants were subjected to a time-course 7 d shade treatment as in (FIG. 5a). Upper panel, top-down view of plant. Lower panel, side view of plant. Scale, 1 cm. FIG. 5c. Ratio of petiole length to leaf blade area in time-course plants (n=3). FIG. 5d. Carotenoids Raman peak of time-course shade treatment in *Arabidopsis* plants in (FIG. 5b) (leaf blade: n=10, petiole: n=8). Bars and graph denote average±SE. Statistical significance between control and different durations of shade treatment was determined by Student's t-test: *, $P<0.05$; , $P<0.01$; *, $P<0.001$.

FIG. 7a. Phenotype of plants at different age and different durations of shade treatment. 10 d-old plants were subjected to 7 d treatment of white light (WL) or deep shade (DS). FIG. 7b. Carotenoids Raman peak of plants in (FIG. 7a). Dashed line indicates difference in peak intensity between WL and DS. DAG, days after germination.

FIG. 8a. Phenotype of phyB-$9^{BC}$ and phyA-211 after 7 d shade treatment and respective ratios of petiole length to leaf blade area. FIG. 8b. Carotenoids Raman peak of plants in (FIG. 8a) (leaf blade: n=8, petiole: n=4). FIG. 8c. Total carotenoids content (µg/g fresh weight) of plants in (FIG. 8a) (n=3). FIG. 8d. Phenotype of 24 d old WT *Arabidopsis* plants grown in low to high plant density.

Numbers represent plants per pot. Upper panel, individual plants from each pot, from top-down view. Lower panel, individual plants from each pot from side view. Scale, 5 cm. FIG. 8e. Carotenoids Raman peak of *Arabidopsis* under low to high plant density in (FIG. 8d) (leaf blade: n=5, petiole: n=3). Bars denote average±SE. WL, white light; MS, moderate shade; DS, deep shade. Statistical significance between control (WL or 1 plant/pot) and the respective treatment (shade or high planting density) was determined by Student's t-test: *, P<0.05; , P<0.01; *, P<0.001.

FIG. 9a. Petiole length and leaf blade area of phyB-9$^{BC}$ and phyA-211 under shade. Bars denote average±SE (n=3). FIG. 9b. Raman spectra of leaf blades and petioles of phyB-9$^{BC}$ and phyA-211 in (FIG. 9a) (leaf blade: n=8, petiole: n=4). WL, white light; MS, moderate shade; DS, deep shade

FIG. 11a. Phenotype of Kai Lan and Choy Sum in shade conditions. Scale, 5 cm. FIG. 11b. Ratio of petiole length to leaf blade area of plants in (FIG. 11a) (n=3). FIG. 11c. Carotenoids Raman peak of Kai Lan and Choy Sum (Leaf blade: n=8, petiole: n=4). Bars denote average±SE. FIG. 11d. Total carotenoids content (μg/g fresh weight) from Kai Lan and Choy Sum in (FIG. 11a). FIG. 11e. Relative expression of homologues of *Arabidopsis* shade-induced genes in Kai Lan and Choy Sum leaf blades and petioles. X-axis represents duration of exposure to DS (n=3). WL, white light; MS, moderate shade; DS, deep shade. N.D., not detected. Statistical significance between WL and shade was determined by Student's t-test: *, P<0.05; ***, P<0.001.

FIG. 12a. Development of leaf number 1 (blue arrowhead) in vegetables. Scale, 2 cm. FIG. 12b. Measurements of petiole length, leaf blade area, hypocotyl length, and epicotyl length of Kai Lan and Choy Sum grown in shade conditions. Bars denote average±SE (n=3). FIG. 12c. Raman spectra of leaf blades and petioles of Kai Lan and Choy Sum in (FIG. 12a) (leaf blade: n=8, petiole: n=4). WL, white light; MS, moderate shade; DS, deep shade; C, cotyledon FIG. 13a. Phenotype of leafy vegetables under time-course shade treatment. Basic strategy for shade treatment is the same as shown in FIG. 5a. 3-14 d old Kai Lan and Choy Sum plants were grown in WL, followed by shade treatment in DS for 4 h to 14 d. All plants were of same age during measurement of phenotype and Raman spectroscopy. Scale, 5 cm. FIG. 13b. Ratio of petiole length to leaf blade area of plants in (FIG. 13a) (n=3). FIG. 13c. Carotenoids Raman peaks of time-course shade treatment plants in (FIG. 13a) (n=4). Bars and graph denote average±SE. Statistical significance between control and different durations of shade treatment was determined by Student's t-test: *, P<0.05; , P<0.01; *, P<0.001.

FIG. 14a. Raman spectra of leaf blades and petioles of Kai Lan (n=5). FIG. 14b. Raman spectra of leaf blades and petioles of Choy Sum (n=4).

FIG. 15a. Phenotype of Kai Lan and Choy Sum in low to high density conditions (plants/pot). Scale, 5 cm. FIG. 15b. Ratio of petiole length to leaf blade area of leafy vegetables in (FIG. 15a) (n=3). FIG. 15c. Carotenoids Raman peaks of Kai Lan and Choy Sum (leaf blade: n=6, petiole: n=4). Bars denote average±SE. Statistical significance between control (1 plant/pot) and high density planting was determined by Student's t-test: *, P<0.05; **, P<0.01.

FIG. 16a. Measurements of petiole length, leaf blade area, hypocotyl length, and epicotyl length of Kai Lan and Choy Sum grown in low to high density conditions. Bars denote average±SE (n=4). FIG. 16b. Raman spectra of leaf blades and petioles of Kai Lan and Choy Sum in (FIG. 16a) (leaf blade: n=6, petiole: n=4).

FIG. 17a. Phenotype of various plant species grown in shade. Scale, 5 cm. FIG. 17b. Carotenoids Raman peaks of leaf blade and petiole of plants in (FIG. 17a) (Baby Bok Choy: leaf blade n=7, petiole n=4; Bok Choy 'Purple King': leaf blade n=6, petiole n=6; Romaine Lettuce: leaf blade n=6, petiole n=6; *Nicotiana benthamiana*: leaf blade n=3, petiole n=3; *Nicotiana tabacum*: leaf blade n=6, petiole n=3). WL, white light; MS, moderate shade; DS, deep shade. Bars denote average±SE. Statistical significance between WL and shade was determined by Student's t-test: *, P<0.05; , P<0.01; *, P<0.001.

DETAILED DESCRIPTION OF THE INVENTION

Figure 1:
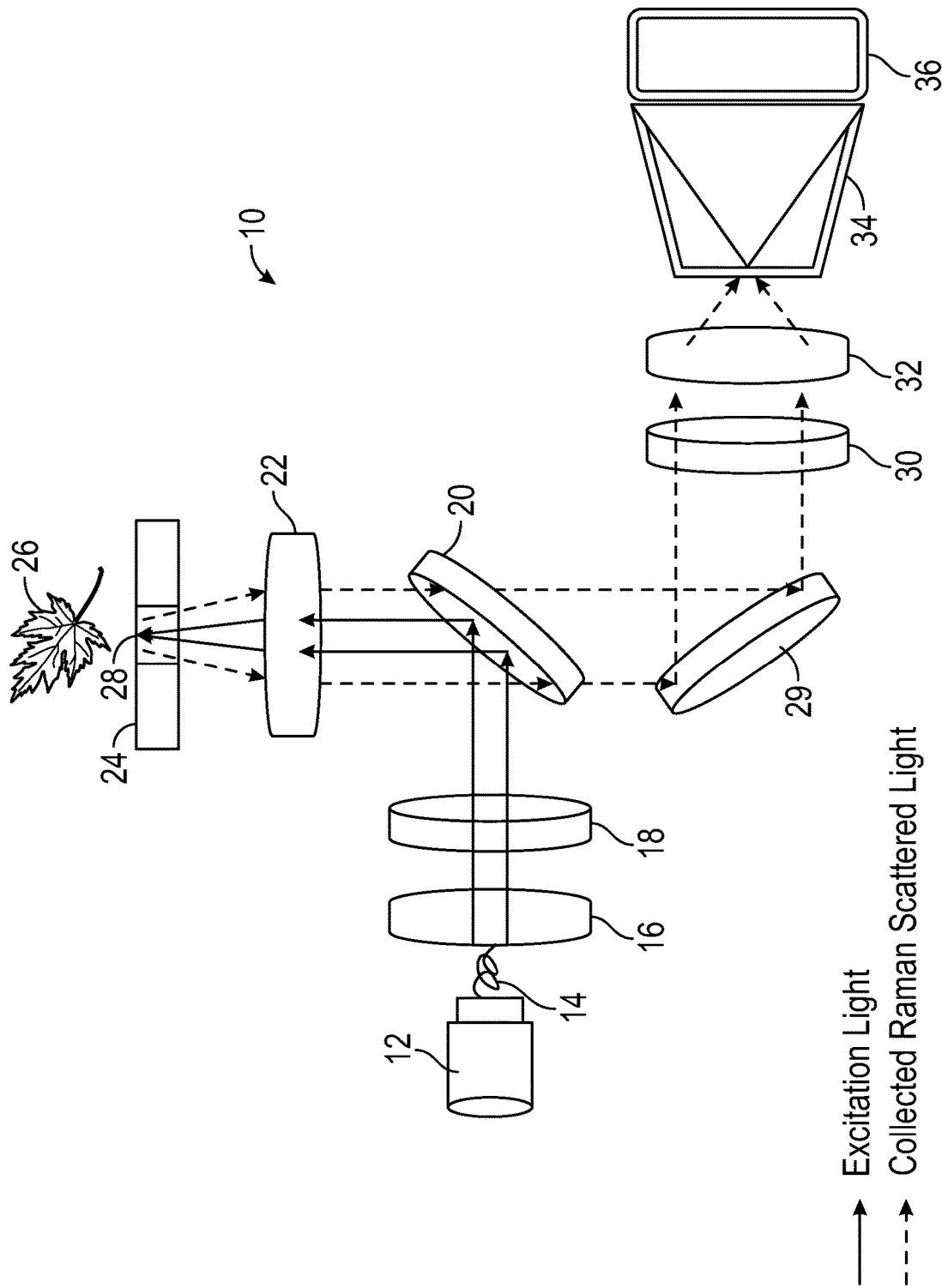
FIG. 1 shows a schematic diagram of purpose-built Raman Spectroscopy system used in the Examples.

The present invention relates to the use of Raman spectroscopy to identify a spectral biomarker that is associated with shade avoidance syndrome (SAS) in plants, which then can be used for the early, real-time diagnosis of SAS in plants and ultimately for slowing or preventing further development of SAS in plants. More specifically, the present invention relates to the use of a Raman spectral signature of plant metabolites, specifically carotenoids, as a biomarker for an early, real-time diagnosis of SAS in growing plants in a non-invasive or non-destructive way in order to detect the adverse effect of the SAS upon their health, and ultimately their yield. The early, real-time diagnosis of SAS provides a window period within which further adverse effects of the SAS may be slowed or prevented without negatively affecting the yield of growing plants or leafy vegetables.

Thus, in one aspect, the present invention provides a method of diagnosing Shade Avoidance Syndrome (SAS) in a plant. In accordance with this aspect, the method comprises:

(a) obtaining a Raman spectra of carotenoids in vivo and in situ in tissue of a plant leaf at a first point in time, wherein the Raman spectra includes one or more peaks characteristic of carotenoids;

(b) obtaining a Raman spectra of carotenoids in vivo and in situ in the tissue of the plant leaf at a second point in time, wherein the Raman spectra includes the one or more peaks characteristic of carotenoids;

(c) comparing intensity of the one or more peaks characteristic of carotenoids from the Raman spectra obtained at the first point of time with intensity of the one or more peaks characteristic of carotenoids from the Raman spectra obtained at the second point of time; and (d) determining if there is a decrease in the intensity of the one or more peaks characteristic of carotenoids from the Raman spectra obtained at the second point in time, wherein a decrease in intensity of the one or more peaks characteristic of carotenoids from the Raman spectra obtained at the second point of time is indicative of SAS.

In some embodiments, the tissue of the plant leaf is a leaf blade or a leaf petiole. In other embodiments, the tissue of the plant leaf is the leaf blade. In some embodiments, the one or more peaks characteristic of carotenoids in the Raman spectra are selected from the group of peaks consisting of 1004 $cm^{-1}$, 1150 $cm^{-1}$ and 1521 $cm^{-1}$. In other embodiments, the Raman spectra is obtained using near-infrared excitation wavelength. In some embodiments, the near-infrared excitation wavelength is 830 nm. In other embodiments, obtaining the Raman spectra is non-invasive and non-destructive to the tissue of the plant leaf.

In another aspect, the present invention provides a method of reversing the development of Shade Avoidance Syndrome (SAS) in a plant comprising: (a) diagnosing SAS in a plant according to the a method described herein; and (b) reducing the amount of shade affecting the plant. In some embodiments, shade is reduced by providing light to the plant. In other embodiments, shade is reduced by trimming nearby plants.

In laser Raman spectroscopy, monochromatic laser light is directed onto a particular material to be tested. A sensitive detection system then detects light returning, or scattered, from the material. The majority of the light returning from the material is scattered elastically at the same wavelength of the original projected laser light. A very small fraction of the light returning from the material is scattered inelastically at a wavelength different from that of the original projected laser light in a manner known as Raman scattering. Raman scattered light is then separated from Rayleigh scattered light with the use of filters, optical gratings, prisms, and other wavelength selection techniques. The energy difference between scattered Raman light and the incident laser light, conventionally represented in wave numbers ($cm^{-1}$), is related to the vibrational, rotational, or librational states, or combinations thereof, of various molecules in the material being evaluated. Each of the peaks in the resulting Raman spectrum corresponds to a particular Raman active vibration of a molecule or a component thereof. The Raman energy shift is independent of the wavelength of the directed laser light. That is, the energy difference corresponding to the elastically and inelastically scattered light for a particular material remains constant for that material. The characteristic results from Raman scattering can be used to locate, identify and quantify concentrations of a material. The absolute intensities of the resulting Raman peaks are directly related to the concentration of the Raman-active molecules in the material.

The present invention relates to the use of Raman spectroscopy to identify a biomarker that is associated with shade avoidance syndrome (SAS) in plants, which then can be used for the early, real-time diagnosis of SAS in plants and ultimately for slowing or preventing further development of SAS in plants. More specifically, the present invention relates to the use of a Raman spectral signature of plant metabolites, specifically carotenoids, as a biomarker for an early, real-time diagnosis of SAS in growing plants in a non-invasive or non-destructive way in order to detect the adverse effect of the SAS on plant health, and ultimately plant yield. The early, real-time diagnosis of SAS provides a window period within which the further adverse effects of the SAS can be slowed or prevented further development without negatively affecting the yield of growing plants, including leafy vegetables.

The early, real-time diagnosis of the SAS provides a window period within which the adverse effects of the SAS can be reversed without negatively affecting the yield of growing plants, or leafy vegetables. Plants affected by the SAS tend to grow long petioles and small leaf-blades thereby reducing the yield in plants, including leafy vegetables. Early diagnosis of SAS enables treating the syndrome in time to slow or prevent further development of SAS, and to ensure yield of plants, including leafy vegetables particularly growing in artificial urban farming settings.

As shown herein, the concentration of carotenoids in leaf tissue is a biomarker for SAS and can be used to monitor the development and progression of SAS, as well as the slowing or preventing of further development of SAS. Carotenoids have been found to exhibit characteristic Raman scattering, the results of which show up in distinct spectral positions, signal strengths, and spectral widths. More specifically, and as shown herein using the described Raman spectroscopy system, carotenoids exhibit strong characteristic Raman scattering signals at 1004 $cm^{-1}$, 1150 $cm^{-1}$ and 1521 $cm^{-1}$. The intensity of the Raman signals are directly related to the concentration of carotenoids. Thus, a decrease in the intensity of the Raman signals is indicative of a decrease in the concentration of carotenoids, and an increase in the intensity of the Raman signals is indicative of an increase in the concentration of carotenoids. As shown herein, a decrease in the concentration of carotenoids is indicative of SAS.

In some embodiments, Raman spectra are collected using a purpose-built Raman spectroscopy system shown in FIG. 1 and described in detail in Example 1. In one embodiment, a Raman spectroscopy system used herein is designed for 830 nm excitation. In general, the sample holder featured a 100 µm thick fused silica sampling window used for both excitation and collection of the Raman signal. An aspheric lens is used to focus the excitation light and collect the Raman scattered light. The lens is chosen with a depth of focus >1 mm so that Raman signal from the entire cross-section of a leaf is collected. The excitation laser used with this system is a fiber coupled laser (Innovative Photonic Solutions, USA) operating at 830 nm delivering approximately 100 mW of laser power to the sample. Light is delivered from the laser to collimating optics via a 105 micron core multimode fiber. The collimated light is passed through a Semrock MaxLine Laser Line 830 filter (Semrock Inc., USA) to remove any amplified spontaneous emission from the laser and any background generated within the delivery fiber. The filtered light is coupled into the optical path of the excitation lens by a Semrock long pass filter (Semrock Inc., USA) operated as a dichroic mirror. Collected light is passed back through the Semrock filter and then through an additional long pass filter to further attenuate Rayleigh scattered excitation light before being delivered to the spectrometer using an F #matching lens. Spectra are acquired using Kymera 328i spectrograph (Andor, UK) employing a 600 g/mm optical grating. While an embodiment of a Raman spectroscopy has been described, it is appreciated that any Raman spectroscopy system, including different excitation laser wavelengths or different excitation and collection optical design, or different Raman signal detector such as photodiodes or CCDs that can focus light on a plant leaf and collect Raman signal can be used for detecting SAS.

In practice, Raman spectra are collected for carotenoids in plant material such as a plant leaf. For each sample of plant leaf, 5 spectra are collected with an integration time of 10 s per sample spot. Cosmic ray events are identified in the 10 s spectra and removed. After cosmic ray removal, the individual 10 s spectra are smoothed across wavelength using the Savitzky-Golay filter function (MATLAB Inc., USA) with a degree of 11. A representative sample spectrum is created by taking the mean value of the five filtered and smoothed spectra at each wavelength. The sample spectrum resulting from this processing contains Raman and fluorescence signal primarily from the leaf. To generate the leaf Raman spectra presented herein any residual fluorescence is removed by performing a positive residual style polynomial subtraction as described in reference (40). Calibration of the Raman shift is performed using a polystyrene sample with a well-known Raman spectrum (41). Raman spectra CCD counts are normalised to the 590 $cm^{-1}$ Raman shift before comparison between samples.

In one embodiment, the concentration of carotenoids is determined within plant material. In some embodiments, the plant material is leaf material. In other embodiments, the leaf is the first true leaf, second true leaf, third true leaf, etc. In some embodiments, the leaf material is a leaf blade. In other embodiments, the leaf material is a leaf petiole. In some embodiments, Raman spectra are collected at two locations per leaf blade. In some embodiments, the locations are one on each side of the midvein of the leaf blade. In other embodiments, a Raman spectrum is collected at one location in the middle of the leaf petiole. Concentration levels of carotenoids can be determined at different times, for example on different days, to follow any changes in the concentration of carotenoids. As shown herein a decrease in the concentration of carotenoids over time is indicative of SAS. Conversely, a stop to the decrease in the concentration of carotenoids over time is an indication that the further development of SAS has been slowed or prevented.

Raman spectroscopy is faster and easier to use than other techniques used to determine concentrations of carotenoids in plant tissues, is non-invasive and not harmful to the plant, allows real-time measurements as plants grow and develop, measures the concentration of carotenoids in vivo and in situ (i.e., in planta) and enables focusing on small parts of plants for the analysis of individual seedlings and specific plant tissues or cells. These benefits of Raman spectroscopy enables the detection of the development of SAS by Raman spectrometry before the onset of any morphological changes in the plants. The early diagnosis of SAS enables slowing or preventing further development of SAS without adverse effects on plant health and plant yield. The development of SAS and slowing or preventing further development of SAS can be detected and/or followed by Raman spectrometry without destroying plant tissue. As shown herein, Raman spectroscopy can be used for early diagnosis of SAS and slowing or preventing further development of SAS in all growing plants, including leafy vegetables.

The early, real-time diagnosis of SAS provides a time window within which the further development of SAS can be slowed or prevented before the occurrence of adverse effects on the plants including the loss of plant yield. The development of SAS can be slowed or prevented by any technique that reduces the amount of shade that the affected plants are receiving. In some embodiments, shade can be reduced by trimming plants that are casting shade. In other embodiments, shade can be reduced by moving growing plants to areas of more light. In some embodiments, shade can be reduced by providing additional light for the growing plants. Reducing or eliminating SAS is particularly beneficial for artificial urban farming settings. High density agriculture in urban farms were found to obtain higher yields than conventional rural farmlands (45). However, high density urban farms are also less energy efficient. One reason is the need for artificial lighting to supplement insufficient or non-existent solar light, such as the use of light emitting diodes (LEDs) to supplement light availability at the bottom of stacked plant growth systems (46). Therefore, early detection of SAS in such low-light and SAS-prone conditions would benefit agricultural yield.

Figure 8:
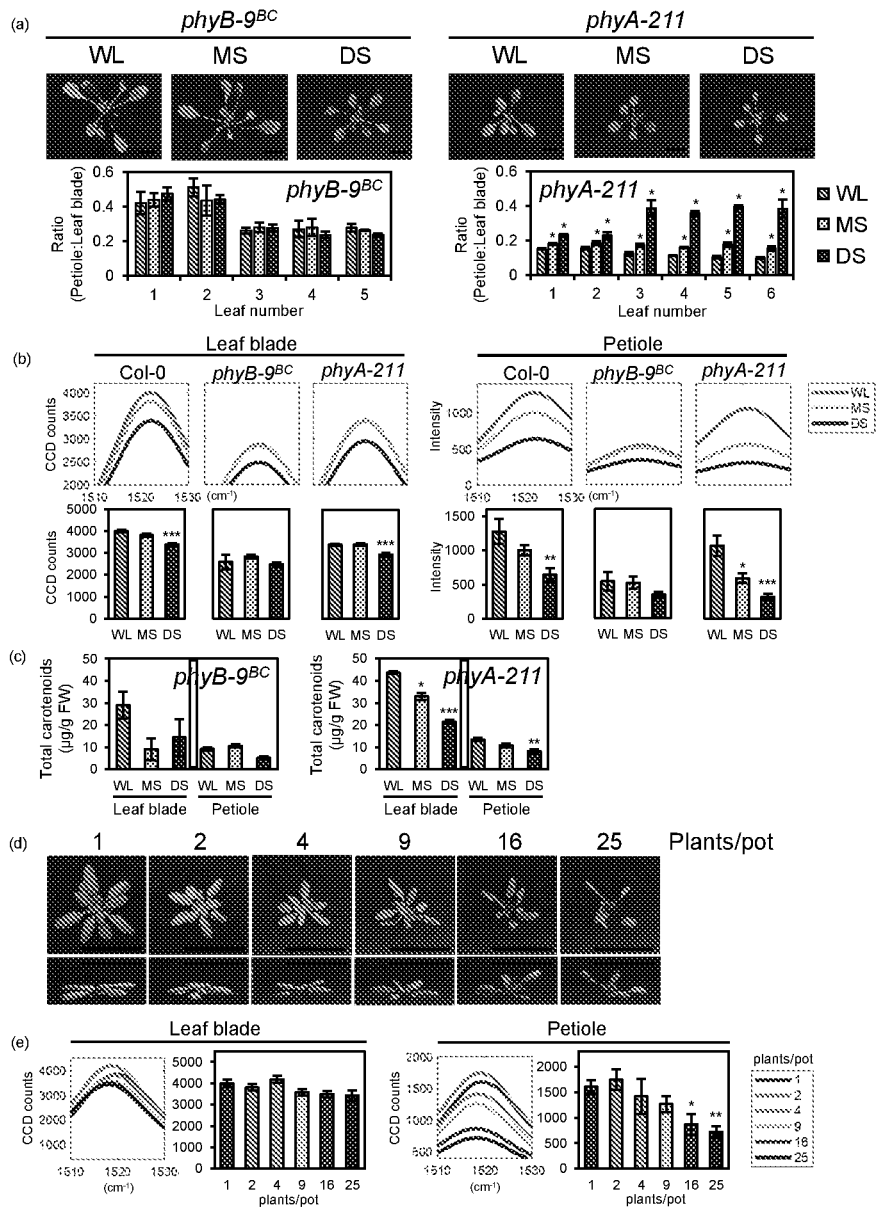
FIGS. 8a-8e show Raman spectra analysis of WT *Arabidopsis* and phytochrome mutants, and of WT *Arabidopsis* at high density planting.
Figure 11:
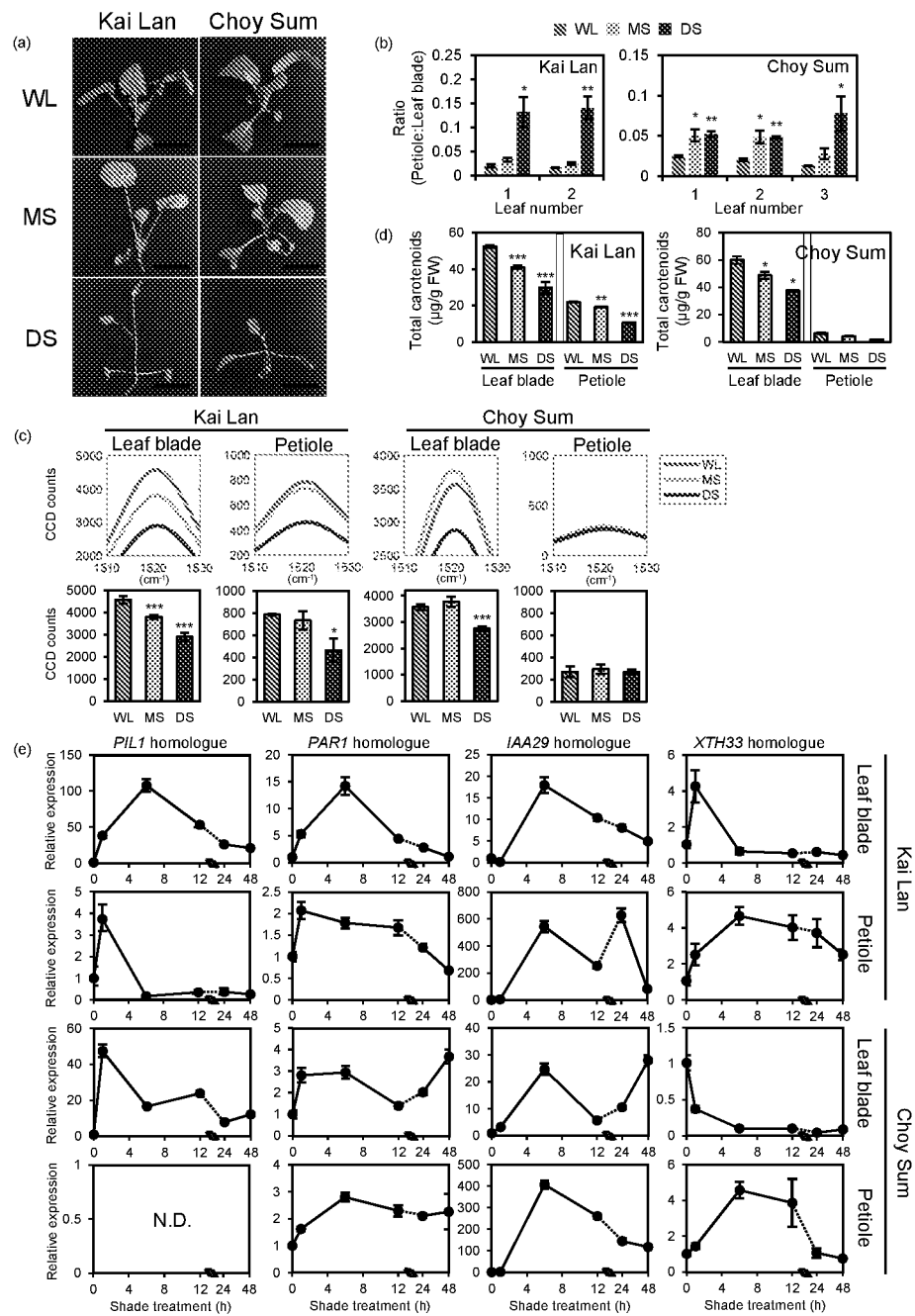
FIGS. 11a-11e show Raman spectra analysis of leafy vegetables under shade.
Figure 12:
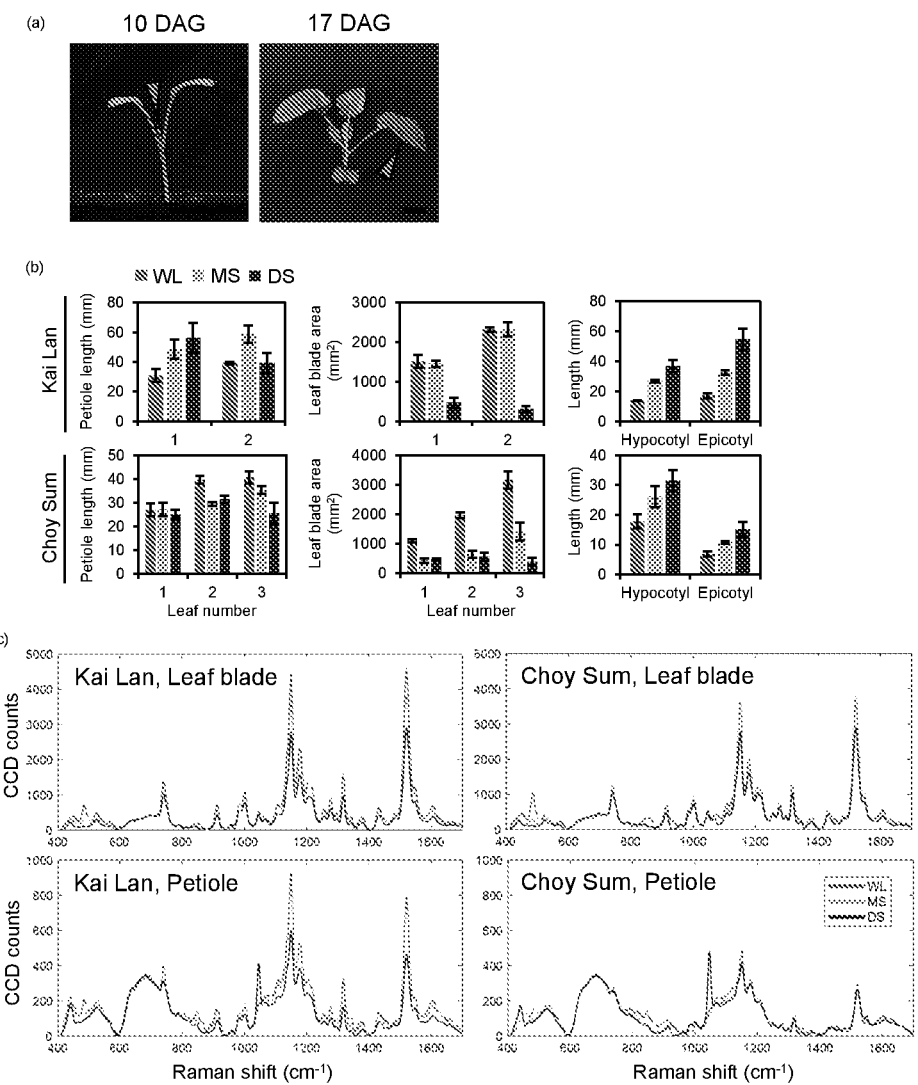
FIGS. 12a-12c show Raman spectra of leafy vegetables under shade conditions.
Figure 17:
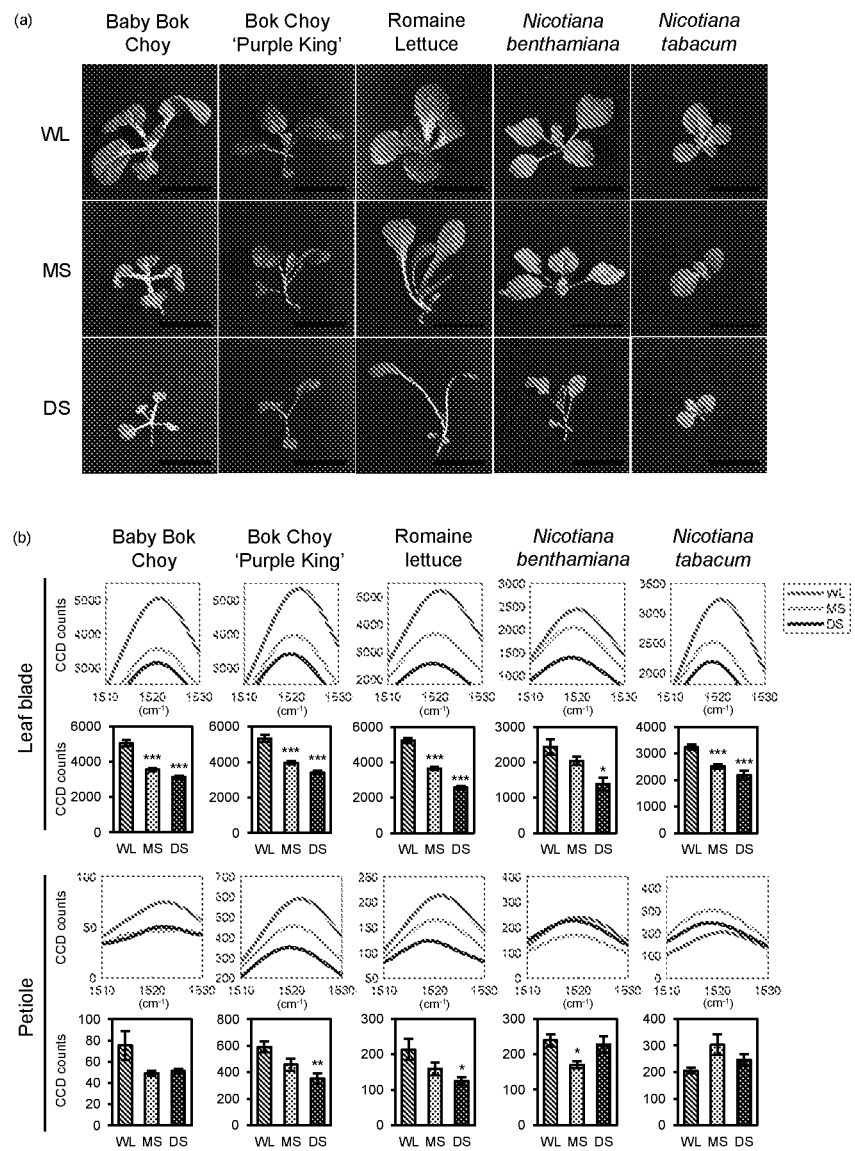
FIGS. 17a-17b show Raman spectra of various plant species under shade conditions.

In the Examples herein, it is shown that the decrease of total carotenoids in plants, which is indicative of SAS, can be detected by Raman spectroscopy as three major peaks in the Raman spectra (1004 $cm^{-1}$, 1150 $cm^{-1}$ and 1521 $cm^{-1}$). While a previous study showed the potential of Raman spectroscopy in identifying general abiotic stress in *Coleus* lime (21), multiple plant species and experimental methods were used in the Examples to demonstrate total carotenoids as a Raman spectroscopy biomarker for SAS. In agreement with a previous report (25), the Examples confirm that the total carotenoids content was reduced during SAS in *Arabidopsis* plants (FIGS. 2d, 8c), as well as in *Brassica* vegetables (FIG. 11d). Likewise, the 1521 $cm^{-1}$ carotenoids peak intensity decreased under shade for all plants with SAS (FIGS. 2, 5, 8, 11, 13, 15, 17)). Although the 1521 $cm^{-1}$ peak is known to overlap with Raman signals of anthocyanins (34), the changes to 1150 $cm^{-1}$ and 1521 $cm^{-1}$ carotenoids peaks were similar in all of the experiments, showing that the results were not affected by the overlap. The results show that the change in carotenoids content is correlated with the development of typical SAS such as shade-induced petiole elongation and inhibition of leaf blade expansion. This finding is supported by the observation that *Arabidopsis* phyB-$9^{BC}$ mutant, having constitutive SAS, showed very low carotenoids peak intensities that did not change in leaf blades and petioles regardless of shade (FIG. 8b). Similarly, petioles of Choy Sum and tobacco species, which did not significantly elongate under shade, showed minimal changes in carotenoids peak intensity (FIGS. 11, 17, 12). All other plant samples which showed SAS under shade display a corresponding decrease in carotenoids peak intensity. These changes are verified by quantification of extracted total carotenoids (FIGS. 2d, 8c, 11d) and the reduced expression of carotenoids biosynthesis genes in shade (FIG. 2f).

Several techniques including gas chromatography-mass spectrometry (GC-MS), liquid chromatography (LC)-MS, capillary electrophoresis (CE)-MS and nuclear magnetic resonance spectroscopy (NMR) are commonly used in plant metabolomics research. All these widely used techniques require sample preparation which can be laborious and are not suitable for in vivo monitoring of metabolites. Moreover, the variable stability of metabolites means that even minor changes in procedure can have a major impact on the observed metabolome. Using Raman spectroscopy, real-time monitoring of plant metabolites in vivo and in a non-invasive manner can be performed. This was not possible with conventional methods as they required homogenization of plant tissue samples, followed by extraction and quantification of the metabolite (14). As an approach to quantifying plant metabolites, Raman spectroscopy has the following advantages: (1) As each measurement takes only a minute to perform, this method allows for faster and easier quantification per sample. (2) The method is non-invasive and not harmful to the plant, allowing for real-time measurements as a plant grows and develops. (3) Metabolites are measured in vivo and in situ, eliminating bias that may be introduced by the extraction and quantification methods (35). (4) Raman spectroscopy enables focusing on small parts of a plant, allowing for the analysis of individual seedlings and specific tissues or cells.

Figure 2:
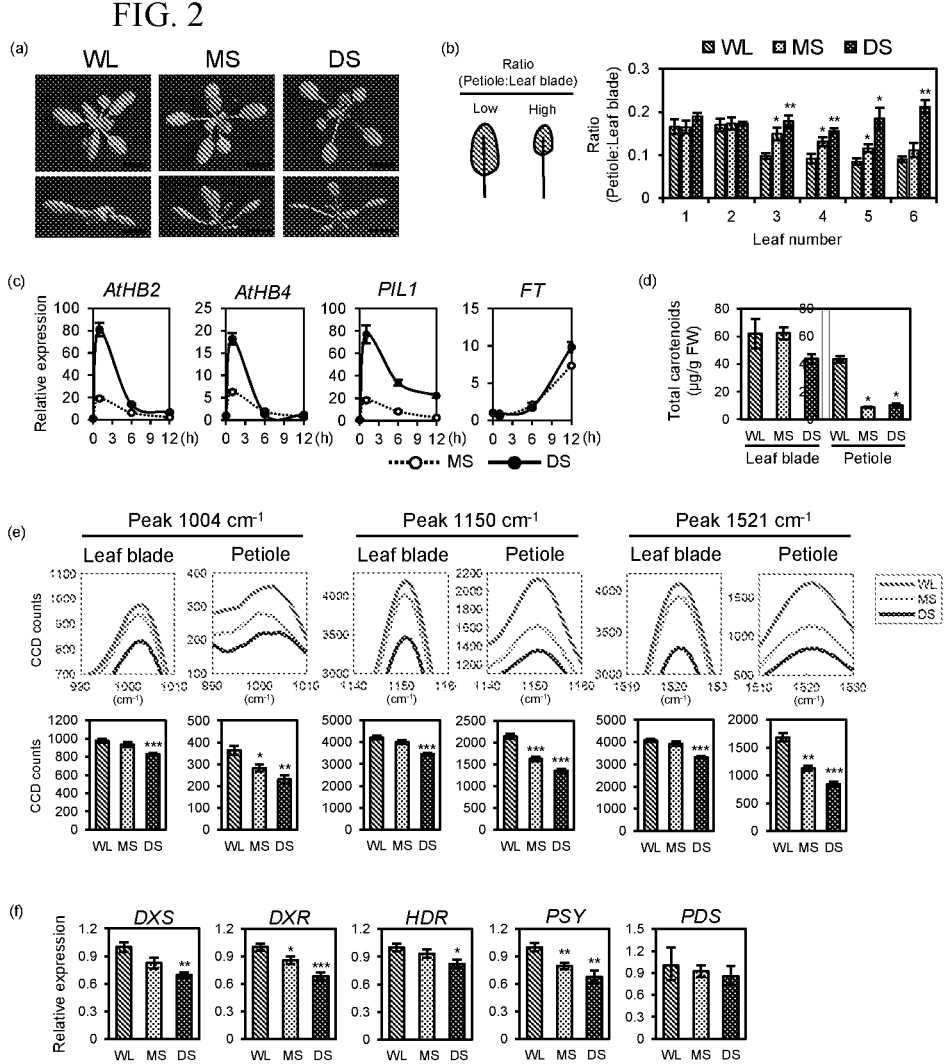
FIGS. 2a-2f show the application of Raman spectroscopy for SAS in *Arabidopsis*.

As the Raman spectroscopy system described herein allows the sampling of small areas on a leaf, it was discovered that the changes in carotenoids peak intensities under shade are remarkably different between leaf blades and petioles, as well as being different between plant species (FIGS. 2, 11, 17). This is supported by shade-related genes responding differently to shade in leaf blades and petioles as shown in FIG. 11e and that different plant species vary in their sensitivity to shade, which ultimately results in different levels of metabolites accumulated during SAS. Separate analysis of leaf blade and petiole metabolite content using a non-invasive method has not been well studied thus far. Hence, the findings herein highlights the importance and applicability of Raman spectroscopy in analyzing the heterogeneity of metabolites within different parts of a plant.

Figure 5:
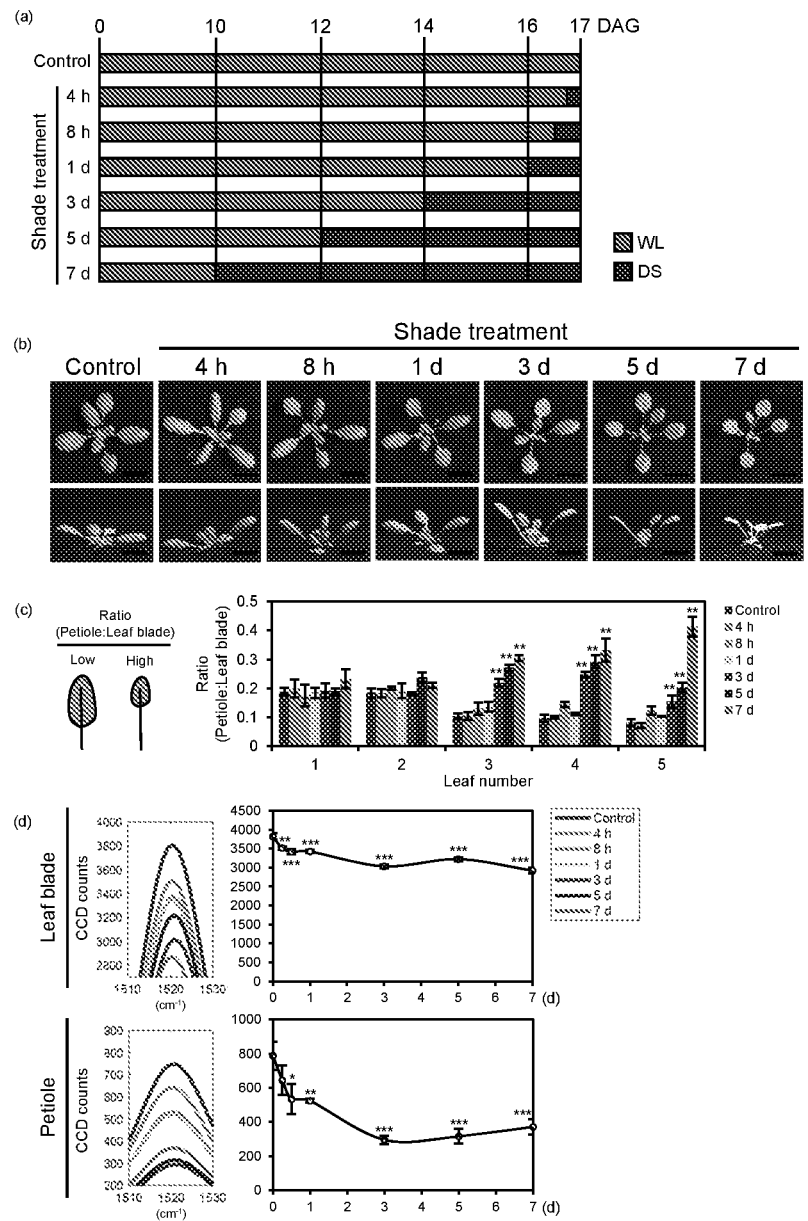
FIGS. 5a-5d show a time-course experiment of SAS using Raman spectroscopy in *Arabidopsis*.
Figure 13:
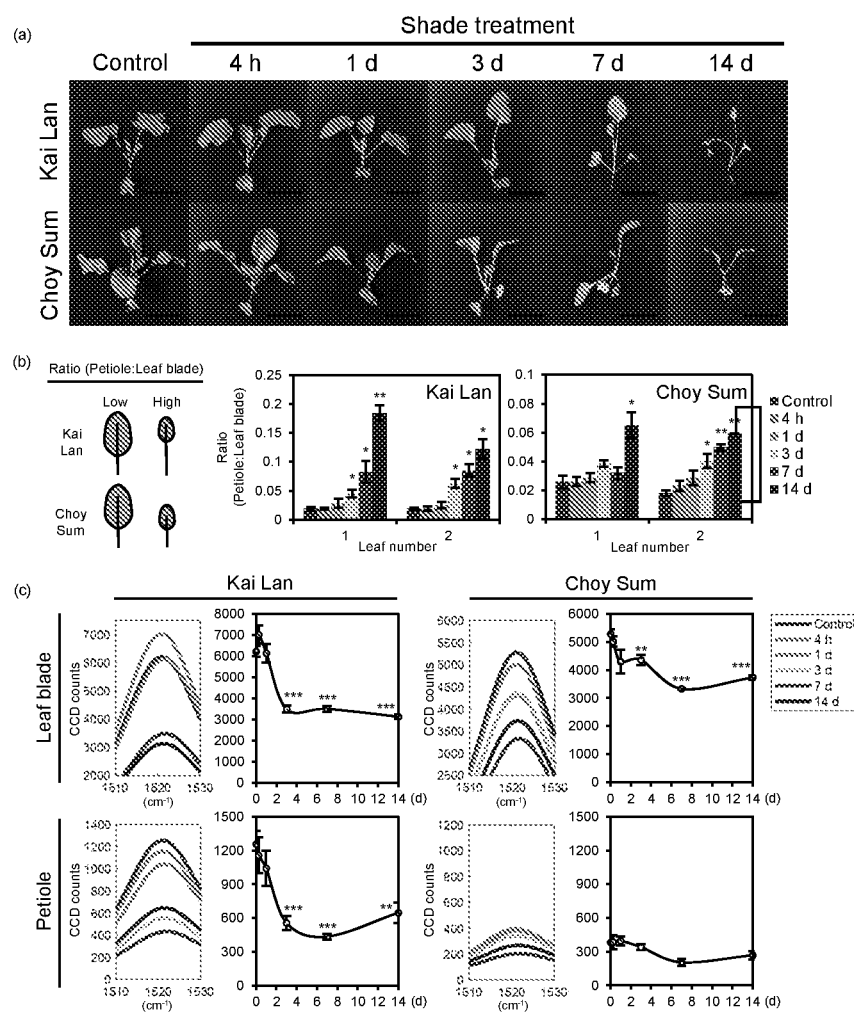
FIGS. 13a-13c show a time-course experiment of SAS in leafy vegetables.

Moreover, the Examples showcases the application of Raman spectroscopy in high-technology urban farms which are required to maximize yield within a limited land space. The Examples show that in all tested plants, the carotenoids Raman peaks respond to shade (FIGS. 2, 11). In addition, these responses are reproducible under natural growing conditions at high plant-density (FIGS. 8, 15), which mimics the situation in high-density farming. Most important, these changes were detected prior to the onset of morphological changes in the plants (FIGS. 5, 13). Taken together, these results show that Raman spectroscopy can be used to monitor individual plants in real-time without homogenizatioin of the plant sample, hence allowing for just-in-time transplanting of crops and maximizing space usage, while minimizing the costs of lighting for growth. It is shown herein that the Raman peak responses may differ between plant species and the duration of shade treatment (FIGS. 5, 13). To address this finding, Raman spectra information of different plant species undergoing SAS can be stored in a database for users to assess their plant's condition. To maximize the use of Raman spectroscopy for diagnosing plant conditions, such as SAS, and high-throughput monitoring of plants, Raman spectroscopy systems can be improved to have more portability, increased sensitivity, and less interference by background fluorescence.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Plant materials and plant growth: Wild-type (Col-0), phyB-9$^{BC}$, phyA-211 was used as *A. thaliana* materials (29,36). All vegetable seeds were purchased from Ban Lee Huat Pte. Ltd. Singapore.

All seeds were subjected to cold stratification at 4° C. in darkness for 3 d before germination and growth in soil at 21° C., 60% relative humidity under long day conditions (16 h light/8 h dark) and in white light (WL) (photosynthetic photon flux density (PPFD)=100 µmol cm$^{-2}$ s$^{-1}$, Red light: far red light (R:FR)=3.0). All seedlings except leafy vegetables were transplanted to individual pots 7 d after germination (DAG), and then subjected to their respective treatments. Leafy vegetable seedlings were transplanted 2 DAG, followed by their respective treatments.

Shade and plant density treatments: Light treatment includes three conditions as follows: WL as a control (PPFD=100 µmol cm$^{-2}$ s$^{-1}$, R:FR=3.0), moderate shade (MS) (PPFD=60 µmol cm$^{-2}$ s$^{-1}$, R:FR=0.7), and deep shade (DS) (PPFD=30 µmol cm$^{-2}$ s$^{-1}$, R:FR=0.2). WL was provided by Panasonic fluorescent tubes FL40SS and FR light was supplemented by CCS Asia ISL-150X150FR light emitting diodes (LEDs) to achieve the R:FR ratios. Top-down lighting was provided in all experiments.

*Arabidopsis thaliana* seedlings at 10 DAG were subjected to 7 d of shade treatment, followed by immediate phenotype measurements or Raman spectroscopy. Vegetable seedlings were grown to 3 DAG, followed by 14 d of shade treatment. *N. benthamiana* and *N. tabacum* seedlings were grown to 10 DAG and subjected to 14 d of shade treatment.

For the plant density experiment, all *A. thaliana*, Kai Lan and Choy Sum seedlings were germinated, grown, and transplanted as described above. Plants were transplanted into different densities and grown until 24 DAG under WL, followed by immediate phenotype measurement or Raman spectroscopy.

Measurement of plant phenotype: Plants were dissected into individual leaves and, if applicable, its stem. Digital photographs of the dissected plant were taken. Petiole length, leaf blade area, and stem length were subsequently measured by using the photographs in ImageJ software (37,38) and Leaf) plugin (39).

Raman system: FIG. 1 is a schematic representation of an exemplary system 10 for collecting Raman spectra data. In general, the system 10 is configured to generate and direct an optical excitation signal of a desired wavelength or wavelength range at a sample specimen, e.g., a leaf, collect Raman scattered light signal from the specimen, direct the collected light signal to a spectrometer to separate and measure spectral components of the collected signal, and record the spectral data.

System 10 includes an excitation laser 12. In one example, the laser operates at 830 nm delivering approximately 100 mW of laser power to the sample. In another example, the laser operates at 830 nm delivering approximately 60 mW of laser power to the sample. A suitable excitation laser is available from Innovative Photonic Solutions, USA.

In the illustrated example, the excitation light signal (solid lines) is delivered from laser 12 to collimating optics 16 (e.g., a collimating lens) via a 105-micron core multimode optical fiber 14, with high optical transmission and low attenuation for laser wavelength range. The collimated light from the collimating optics 16 is passed through a bandpass filter (cleanup filter) 18 to remove any amplified spontaneous emission from the laser 12 and any background generated within the fiber 14. A suitable bandpass filter includes a Semrock MaxLine Laser Line 830 filter (available from Semrock Inc., USA).

The filtered excitation light signal is coupled into an optical path of an excitation lens 22 by a dichroic mirror 20. A suitable dichroic mirror includes a Semrock long pass filter (available from Semrock Inc., USA). The optics including lens and filters are preferably made of fused silica or other low spectral background generating material in the desired Raman signal collection wavelength range.

Excitation light passing through the excitation lens 22 is directed to a sample 26 supported on a sample holder 24, and the Raman scattered signal (dashed lines) is collected by the excitation lens 22 and directed to the dichroic mirror 20. In one example, the excitation lens 22 is an aspheric lens configured to focus the excitation light signal toward the sample 26 and collect the Raman scattered light signal from the sample 26. Excitation lens 22 may have a depth of focus chosen in correspondence to the nature of the sample. In one example, where sample 26 comprises a leaf, excitation lens 22 has a depth of focus greater than 1 mm so that Raman scattered signal from the entire cross-section of the leaf is collected. Sample holder 24 may include a window 28, such as a 100 μm thick fused silica sampling window making the sample as flat as possible and placing it at the correct focal distance from the excitation lens. Through this window, both excitation and collection of the Raman signal is achieved.

The collected Raman scattered light signal is directed by the excitation lens 22 back through the dichroic mirror 20 onto a mirror 29. In the illustrated example, system 10 includes an additional long pass edge filter 30 which attenuates the Rayleigh scattered excitation light wavelength and through which the collected Raman scattered light signal is directed to the spectrometer. 34 before being detected by the charge-coupled device (CCD) camera 36. The long pass edge filter can also be replaced by a suitable notch filter.

The filtered Raman scattered light signal is directed from filter 30 to a spectrometer 34 using an F #matching lens 32. A suitable spectrometer for acquiring spectra includes a Kymera 328i spectrograph (Andor, UK) employing a 600 g/mm optical grating. Spectral data may be recorded by a recording device 36, such as a charge-couple device ("CCD") camera thermoelectrically cooled to −80° C.

Raman spectra collection: For each sample of plant leaf, 5 spectra were collected with an integration time of 10 s per sample spot. Cosmic ray events were identified in the 10 s spectra and removed. After cosmic ray removal, the individual 10 s spectra were smoothed across wavelength using the Savitzky-Golay filter function (MATLAB Inc., USA) with a degree of 11. A representative sample spectrum was created by taking the mean value of the five filtered and smoothed spectra at each wavelength. The sample spectrum resulting from this processing contained Raman and fluorescence signal primarily from the leaf. To generate the leaf Raman spectra presented in the results section any residual fluorescence was removed by performing a positive residual style polynomial subtraction as described in Lieber and Mahadevan-Jansen (40). Calibration of the Raman shift was performed using a polystyrene sample with a well-known Raman spectrum (41). Raman spectra CCD counts were normalised to the 590 cm$^{-1}$ Raman shift before comparison between samples.

Plant samples for Raman Spectroscopy: For *A. thaliana*, to ensure that the leaf received the full shade treatment, leaf blades and petioles of the third true leaf were used for measuring the Raman spectrum. Similarly, for Kai Lan and Choy Sum, leaf blades and petioles of the first true leaf were chosen for Raman spectroscopy.

The Raman spectra were measured from two locations per leaf blade (one on each side of the midvein) and one location in the middle of the petiole. A minimum of three biological replicates were used per plant sample. Student's t-test was used to determine P-values.

RNA extraction and quantitative reverse transcriptase polymerase chain reaction (qRT-PCR: Total RNA was extracted from finely ground plant samples using Ribospin Plant (GeneAll). The concentration of extracted RNA was determined by using NanoDrop 2000 Spectrophotometer (Thermo Fisher Scientific). Reverse transcription was performed using M-MLV reverse transcriptase (Promega).

Relative gene expression were quantified by 7900HT Fast Real-Time PCR system (Applied Biosystems). The reaction mixture consists of TB Green® Premix Ex Taq™ (Tli RNase H Plus) ROX Plus (TaKaRa), cDNA from plant samples, and primer pairs in Table 1.

TABLE 1

Primer Pairs for qRT-PCR Analysis

*Arabidopsis thaliana*

| Gene | Forward primer (5'-3') (SEQ ID NO:) | Reverse primer (5'-3') (SEQ ID NO:) |
|---|---|---|
| AtHB2 | CATGAGCCCACCCACTACTT (1) | ACCTAGGACGAAGAGCGTCA (2) |
| AtHB4 | GAACGTGTCTCCTCCTCTGC (3) | CCTAGCGACCTGATTTTTGC (4) |
| PIL1 | CAGCAACACCAACATCAATAC (5) | TGGAATTAGTCCACTTGGGTG (6) |
| FT | CTAGCAACCCTCACCTCCGA (7) | TCGTAACACACAATCTCATTGCCAAA (8) |
| DXS | TCGCAAGGGTATGACAAAG (9) | CAGTCCCGCTTATCATTCC (10) |
| DXR | TTGGGTTGGCCTGATATGCG (11) | AGTCATTGTGCCTCCAGCTC (12) |
| HDR | TTCGAAGGGTTTCGATCCCG (13) | TTGCGTCTTGTCGCTCTTGA (14) |
| PSY | GACACCCGAAAGGCGAAAGG (15) | CAGCGAGAGCAGCATCAAGC (16) |
| PDS | GTCGGTCACGCGCTCAGGTA (17) | CGAGATGCTGACATGGCCAGA (18) |
| UBQ11 | GCAGATTTTCGTTAAAACC (19) | CCAAAGTTCTGCCGTCC (20) |

TABLE 1-continued

Primer Pairs for qRT-PCR Analysis

Kai Lan (*Brassica oleracea* var. *alboglabra*)

| Gene (Homologue) | Forward primer (5'-3') (SEQ ID NO:) | Reverse primer (5'-3') (SEQ ID NO:) |
|---|---|---|
| Bol004887 (PIL1) | TATCATTGCTGGACGAGGCG (21) | CTGCGCCCATATGCATTCCT (22) |
| Bol021572 (PAR1) | GGTGGTTTCGAACGCAGAAC (23) | TTCTTCTTGGCCGGAGACAC (24) |
| Bol033768 (IAA29) | GGACTTAGACCGTCATCGTCA (25) | GGTAATAGCCAGTCGCCCTC (26) |
| Bol022041 (XTH33) | TCGCCAAACTCACTCTCGAC (27) | ACCACAACACCAGAGGCAAA (28) |
| Bol030974 (ACTIN2) | CATGTTCACCACAACAGCCG (29) | AGTCTCCATCTCCTGCTCGT (30) |

Choy Sum (*Brassica rapa* var. *parachinensis*)

| Gene (Homologue) | Forward primer (5'-3') SEQ ID NO:) | Reverse primer (5'-3') (SEQ ID NO:) |
|---|---|---|
| Brara.C02346 (PIL1) | GGTTTTCCCCGGATCAACGA (31) | CACGAAGGCACGACGAATTG (32) |
| Brara.E00305 (PAR1) | TTTGAGCGCAGAACCAAACG (33) | AATCCTCTGCAACGCCTCAA (34) |
| Brara.K00374 (IAA29) | GGACTTAGACCGTCATCGTCA (35) | GGTAATAGCCAGTCGCCCTC (36) |
| Brara.H02756 (XTH33) | TTTGCCTCTGGTGTTGTGGT (37) | ACTCTATGTCTATCTCATCGTGGGT (38) |
| Brara.A02909 (ACTIN2) | CATGTTCACCACAACAGCCG (39) | AGTCTCCATCTCCTGCTCGT9 (40) |

*A. thaliana* gene sequences were referenced from TAIR (42), and gene expression was normalized to UBQ11 as the internal control. Reference gene sequences for Choy Sum (*Brassica rapa* FPsc v1.3) and Kai Lan (*Brassica oleracea capitata* v1.0) were obtained from Phytozome (43). Homologues with the highest similarity to *Arabidopsis* genes were selected and gene expression was normalized to homologues of *Arabidopsis* ACT2.

Measurement of total carotenoids content by ultraviolet-visible (UV-VIS) spectrophotometer: Plant samples were frozen in liquid nitrogen and ground into a fine powder before extraction. Fresh weight was measured and used for normalization between samples. To extract total carotenoids, 100 mg fresh weight of the sample was resuspended in 1 mL of 100% methanol and kept on ice in darkness for 20 min. After centrifugation at 16,000 g at 4° C. for 4 min, the supernatant was transferred to a separate tube. Sample extractions were repeated until the sample loses all coloration. All extracts were pooled together. Absorbance values at 470 nm, 653 nm, and 666 nm were measured using Spark multimode microplate reader (Tecan) and total carotenoids were calculated based on the formula by Wellburn and Lichtenthaler (44).

Example 2

Raman Spectra Analysis of Shade Avoidance Syndrome (SAS)

Figure 3:
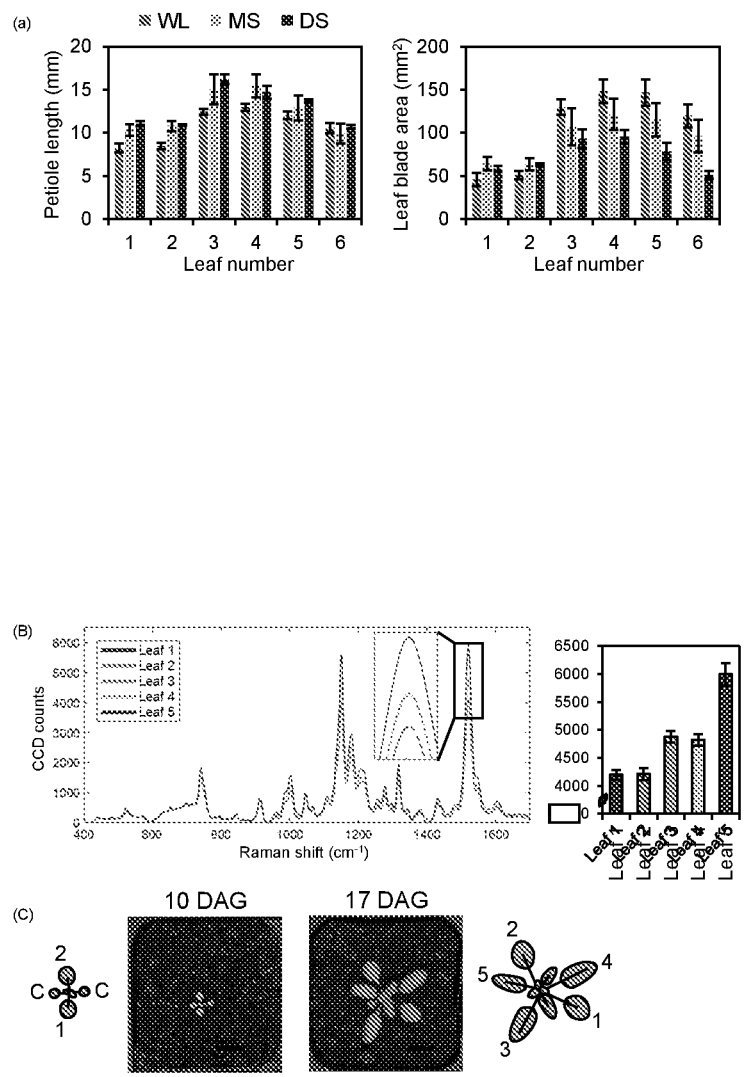
FIGS. 3a-3c show the verification of shade conditions and determining leaf number of *Arabidopsis* plant for Raman spectroscopy.

To investigate if Raman spectroscopy could identify metabolites that change in response to shade, shade conditions were established that were low in Red:Far-red (R:FR) light to induce SAS in *Arabidopsis* plants. Wild-type (WT, Col-0) *Arabidopsis* seedlings (10 DAG) were grown under three different light conditions: white light (WL) for normal growth of *Arabidopsis*, moderate shade (MS) for partial vegetative shade, and deep shade (DS) for severe shade for 7 d. FIGS. 2a, 2b, 3a show that MS condition reproducibly induced typical SAS in WT, including hyponasty of rosette leaves, reduction of leaf blades, and elongation of petioles. SAS became more obvious in DS condition, showing that our shade setup can dynamically induce SAS (FIGS. 2a, 2b, 3a). These morphological changes were accompanied by the expression of shade-induced marker genes such as *A. thaliana* Homeobox Protein 2/4 (AtHB2/AtHB4) and Phytochrome Interacting Factor 3-Like 1 (PIL1), which were highly induced under short durations of MS and DS treatment (FIG. 2c) (6,22). Likewise, the induction of the flowering gene Flowering Locus T (FT) in shaded conditions indicated the early flowering of SAS plants (FIG. 2c) (23).

A tabletop Raman spectroscopy instrument with specific near-infrared (830 nm) excitation wavelength was built. As light signaling in plants involves perception and response to visible light, we chose the 830 nm excitation laser to avoid activating any light signaling pathways. Moreover, this wavelength of light was found to provide the largest signal-to-background of the various excitation wavelengths considered (450-830 nm). The optical background here was dominated by off-resonant chlorophyll autofluorescence excited by the infrared laser. This infrared excitation wavelength falls within a spectral window of very low optical absorption in most plant leaves, resulting in neglible photodamage to the plant tissues or metabolites even if the laser fluence used is 100 times stronger compared to that used previously (24).

Using the purpose-built Raman spectroscopy system (FIG. 1), changes of metabolites in each rosette leaf of WT *Arabidopsis* were investigated. Basically, the spectra intensities were low in the old leaves and increased in accordance to their leaf number (FIG. 3b). This suggests that the metabolites in the leaf become less concentrated as the leaf ages. During the aforementioned shade treatment, ten day-old *Arabidopsis* plants were subjected to shade treatment for 7 d, which exposed the third rosette leaf to the full duration of shade treatment during its development (FIG. 3c. Hence, to ensure that the sampled leaf accurately represented the effect of the shade treatment, the third rosette leaf was chosen for all further Raman spectroscopy measurements.

Figure 4:
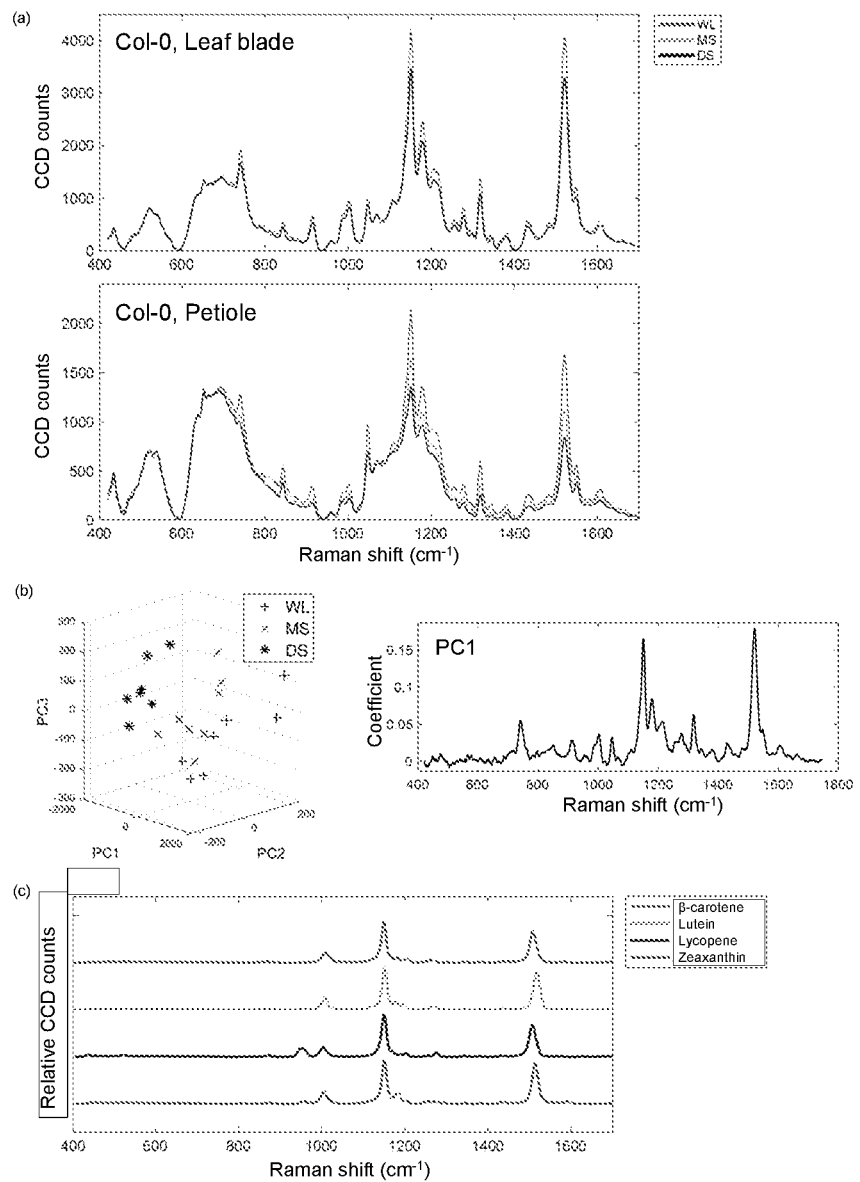
FIGS. 4a-4c show Raman spectra of *Arabidopsis* plant under shade conditions.

The spectra obtained for *Arabidopsis* under the two shade treatments (WL, MS, DS) showed the same spectral pattern and peak numbers (FIG. 4a). No additional or missing peaks were found within the scope of metabolites measured by the current Raman system. However, it was noted that the intensity of most peaks above 700 $cm^{-1}$ Raman shift decreased under shade conditions. This result is consistent with previous studies, which showed that the levels of multiple metabolites decreased under shade (10,11).

To identify the peaks with the largest change under shade conditions, a principal component analysis (PCA) plot was performed using these data (FIG. 4b). As an additional verification of metabolite changes under shade, the clustering of points were clearly separated in WL and DS, while clustering of MS was an intermediate between WL and DS. By plotting the PCA coefficients against Raman shift, the peaks at 1150 $cm^{-1}$ and 1521 $cm^{-1}$ Raman shift were identified as the largest change under shade (PC1) (FIG. 4b). Based on our Raman spectrum library of chemical standards, the 1150 $cm^{-1}$ and 1521 $cm^{-1}$ peaks were identified to be present in all tested carotenoids (FIG. 4c). Furthermore, the carotenoid standards share a third Raman peak at 1004 $cm^{-1}$ Raman shift (FIG. 4c). Previous studies have already established that shade condition reduces carotenoids biosynthesis and the total carotenoids content in leaves (25), thereby supporting the observations here. For verification, total carotenoids in our samples were extracted and quantified using conventional UV-VIS spectroscopy and found similar results (FIG. 2d).

FIG. 2e shows that in *Arabidopsis* plants, the total carotenoids peaks (1004 $cm^{-1}$, 1150 $cm^{-1}$ and 1521 $cm^{-1}$) highly decreased in DS in both leaf blade and petiole. All peaks have similar decrease in intensity: in leaf blades, the 1004 $cm^{-1}$ peak decreased by 4% in MS and 15% in DS, the 1150 $cm^{-1}$ peak decreased by 5% in MS and 18% in DS, and the 1521 $cm^{-1}$ peak decreased by 4% in MS and 19% in DS (FIG. 2e). Interestingly, shade caused a greater decrease in peak intensity for carotenoids and other peaks in the petioles than in leaf blades (FIGS. 2e, 4a), as the 1004 $cm^{-1}$ peak decreased 22% (MS) and 37% (DS), the 1150 $cm^{-1}$ peak decreased by 24% (MS) and 37% (DS), and the 1521 $cm^{-1}$ peak decreased by 33% (MS) and 50% (DS), suggesting that more metabolomic changes occurred in the petioles during SAS (FIG. 2e). As all peaks showed similar trend under shade and the 1521 $cm^{-1}$ peak was less affected by autofluorescence, subsequent experiments focused on the 1521 $cm^{-1}$ peak as a representative of carotenoids peaks.

To further verify the decreased carotenoids content in shade conditions, we measured the expression of genes related to carotenoids biosynthesis, which are known to be down-regulated in etiolated plants (26). Expression levels of upstream methylerythritol 4-phosphate (MEP) pathway genes (1-deoxy-D-xylulose-5-phosphate synthase, DXS; 1-deoxy-D-xylulose 5-phosphate reductoisomerase, DXR; hydroxymethylbutenyl 4-diphosphate reductase; HDR) and the first commited step of carotenoids biosynthesis (Phytoene Synthase, PSY) were down-regulated under shade conditions, with lower gene expression in more severe shade conditions (FIG. 2f). As such, the decreased intensity of carotenoids peaks under shade correlates with the decrease in carotenoids content. These results show that Raman spectroscopy can detect SAS caused by vegetative shade.

Example 3

Early Diagnosis of SAS Using Raman Spectroscopy

Figure 6:
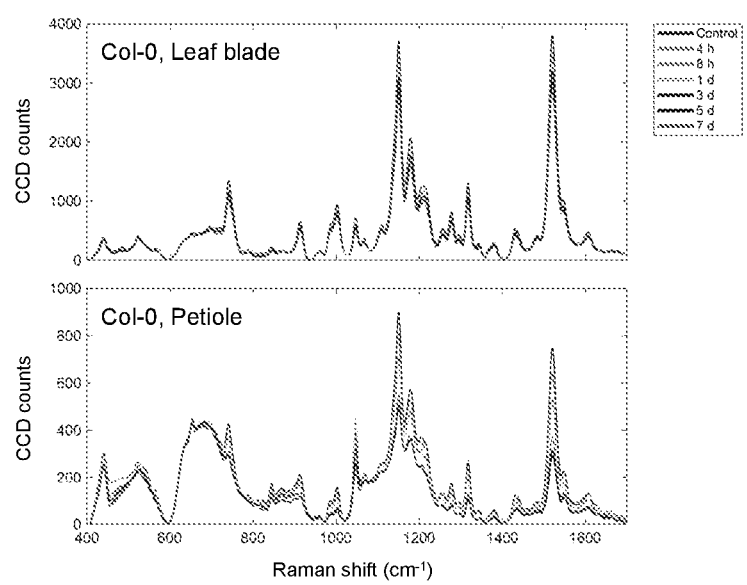
FIG. 6 shows Raman spectra of same-age wild type (Col-0) *Arabidopsis* plants with different duration of shade treatment. Number of hours (h) or days (d) represents the duration of shade treatment. Control plants are not exposed to shade. (leaf blade: n=10, petiole: n=8.
Figure 7:
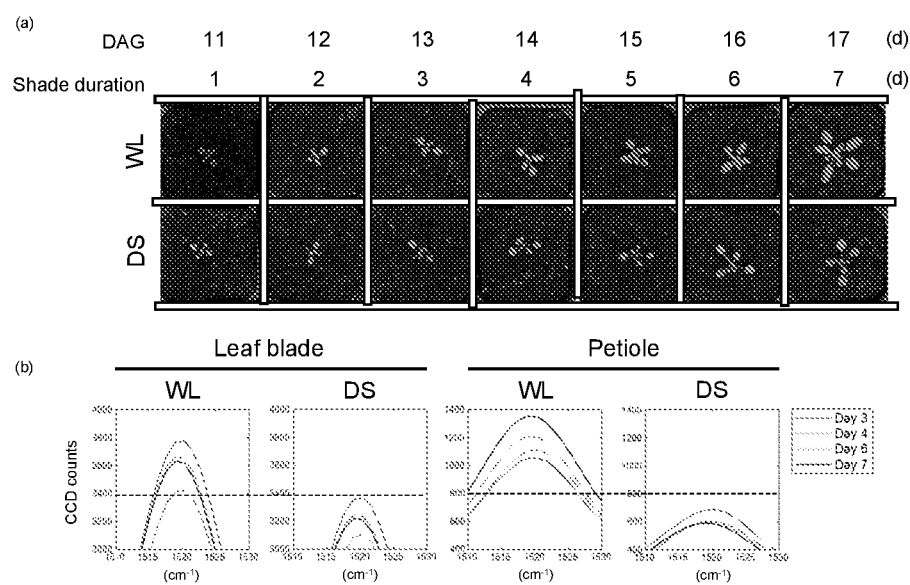
FIGS. 7a-7b show Raman spectra of *Arabidopsis* plants from seedling to mature stage in time-course shade experiment.

After establishing that the carotenoids Raman peaks are indicative of SAS, we then asked if these metabolites would respond early to shade. WT *Arabidopsis* plants were subjected to different durations of DS treatment before measuring their Raman spectra (FIG. 5a). With longer exposure to shade, the plants developed more severe SAS, with morphological changes after 1-3 d of shade treatment (FIG. 5b, 5c). Furthermore, morphological changes affected leaf number 3 onwards, verifying the measurement of the third rosette leaf in Raman spectroscopy (FIG. 5c). Surprisingly, changes in the carotenoids peak intensities were detected much earlier, starting from just 4 h of DS condition (FIG. 5d, 6). Carotenoids peak in both leaf blades and petioles decreased between 4 h to 3 d of shade treatment, reaching a steady state level 3 d onwards (FIG. 5d). Similar with the results thus far, there is a larger decrease in peak intensity in the petioles (18% at 4 h to 53% at 7 d) compared to the leaf blades (8% at 4 h to 24% at 7 d), confirming that petioles are more reactive to shade. As an additional verification, another time-course experiment was designed, which tracked the daily development of SAS and Raman peak changes under WL and DS (FIG. 7a). Similar results verified that prolonged shade treatment caused a large decrease in the carotenoids peak intensities, especially in the petioles (FIG. 7b). Together, these results highlight that the intensity of carotenoids peak responded quickly to shade and occurred before obvious morphological changes. These results showed that carotenoids Raman peaks could be used as an indicator for early diagnosis of SAS.

Example 4

Detection of Phytochrome-Mediated SAS by Raman Spectroscopy

It is well known that SAS is mediated by phytochrome signaling, which have photo-reversible activation and inactivation based on the ratio of R and FR light (27). Among the five *Arabidopsis* phytochromes (PHYA-PHYE), PHYA and PHYB are regarded as key players in regulating SAS (27). Under high R:FR PHYB is the predominant phytochrome that prevents SAS such as petiole elongation and reduction of leaf blade area, whereas under low R:FR PHYA blocks the excessive elongation of seedlings (27,28).

Figure 9:
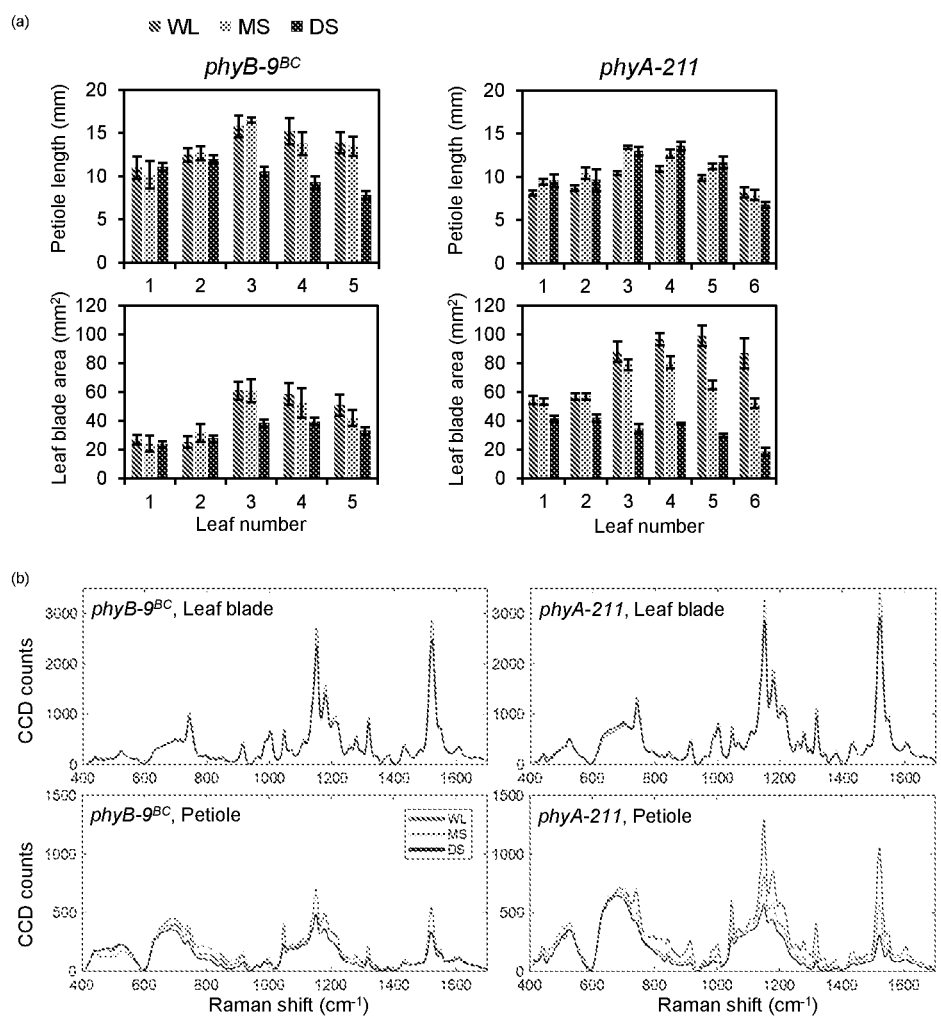
FIGS. 9a-9b show Raman spectra of *Arabidopsis* phytochrome mutants under shade conditions.

To investigate if the decreased intensity of carotenoids Raman peaks during SAS is associated with phytochrome signaling, *Arabidopsis* phytochrome mutants, phyB-$9^{BC}$ and phyA-211, were used to measure their Raman spectra under shade conditions (28,29). Consistent with previous studies, phyB-$9^{BC}$ displayed constitutive SAS, whereas phyA-211 showed no SAS under WL but more severe SAS than WT when under shade (FIGS. 8a, 9a) (1,28,29,30). FIGS. 8b and 9b show that under all growth conditions, phyB-$9^{BC}$ displayed similar and very low intensities for carotenoids Raman peaks, reflecting its constitutive SAS. In phyA-211, the carotenoids peaks in leaf blade and petioles decreased in MS and DS, following a similar trend as WT in shade (FIGS. 8b, 9b). However, phyA-211 has lower intensities than WT under all conditions and phyA-211 petioles have a larger decrease in intensity (45% in MS, 70% in DS) than WT petioles (22% in MS, 50% in DS) (FIG. 8b). The loss of PHYA causes a greater sensitivity to SAS, as PHYA senses low R:FR light and reduces the severity of SAS (28). Extraction of total carotenoids further verified the changes observed in the carotenoids Raman peaks (FIG. 8c). Therefore, these results show that the decrease in carotenoids peaks is caused by phytochrome-mediated SAS and hence could be used as a direct indicator of SAS.

Example 5

Raman Spectra Analysis at High Density Planting

Figure 10:
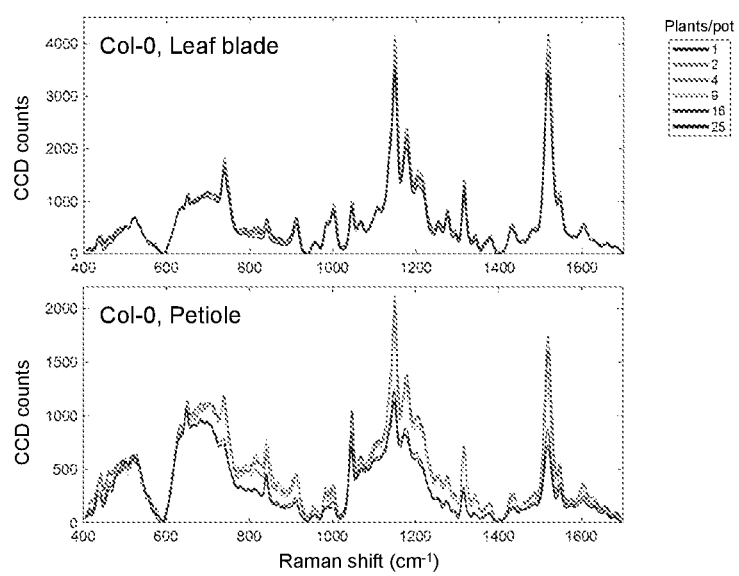
FIG. 10 shows Raman spectra of wild type (Col-0) *Arabidopsis* leaf blades and petioles in low to high density planting. (leaf blade: n=5, petiole: n=3).

Besides vegetative shade, high density planting also causes low R:FR light, inducing SAS (31). To further verify the results obtained from the shade experiment, *Arabidopsis* plants were planted from low to high densities and measured their Raman spectra. FIG. 8d shows that high plant densities (9-25 plants/pot) resulted in an increasingly severe SAS in the *Arabidopsis* plants. The measured Raman spectra reflected this change in SAS, as the carotenoids peak had lower peak intensities at higher planting densities (FIGS. 8e, 10). Similar to the shade treatment results, the peak intensities in the petioles showed more significant decrease (55% decrease in 25 plants/pot) than those in the leaf blades (14% decrease in 25 plants/pot) (FIG. 8e). These results show that the carotenoids peak in Raman spectra can also be used as a marker to detect SAS caused by high-density planting conditions in *Arabidopsis*.

Example 6

Raman Spectra Analysis of Leafy Vegetables Under Shade Conditions

To further validate the use of Raman spectroscopy in SAS, its application in *Brassica* species was investigated. Two species of leafy vegetables, Kai Lan (*Brassica oleracea* var. *alboglabra*) and Choy Sum (*Brassica rapa* var. *parachinensis*) were treated under shade for 14 d. While Kai Lan reacted to the shade conditions with both reduction of leaf blades and elongation of petioles, Choy Sum under shade developed reduced leaf blades but no significant change in petioles (FIGS. 11a, 11b, 12b).

Raman spectroscopy was applied to the first true leaf of vegetables as it received the full duration of shade treatment (FIG. 12a). FIGS. 11c and 12c showed that the carotenoids peak of Kai Lan leaf blade and petiole decreased under both MS and DS (leaf blades, 17% and 37%; petioles, 7% and 41%, respectively). While Choy Sum leaf blades decreased their carotenoids peak intensity by 23% in DS, its petioles had no significant change regardless of the shade condition (FIGS. 11c, 12c). This result might explain the lack of petiole elongation in Choy Sum compared to Kai Lan, especially in the true leaves (FIGS. 11a, 11b, 12b). The reduction in extracted total carotenoids in Kai Lan and Choy Sum under shade was verified by measuring total carotenoids content in homogenized plant tissues (FIG. 11d). Similar to Raman peak intensities, carotenoids content in petioles of Choy Sum was relatively very low compared to those of Kai Lan (FIGS. 11c, 11d). Together, these results showed that SAS in Kai Lan is similar to *Arabidopsis*, whereas only Choy Sum leaf blades but not petioles respond to shade. Importantly, these differences can be clearly detected by measuring the carotenoids Raman peak, making it a useful diagnostic tool in these *Brassica* species.

To further investigate the difference between leaf blades and petioles of Kai Lan and Choy Sum during SAS, we measured the expression of homologues of *Arabidopsis* shade-induced marker genes (PIL1; PAR1, Phytochrome Rapidly Regulated 1; IAA29, Indole-3-acetic acid Inducible 29; XTH33, Xyloglucan:xyloglucosyl Transferase 33), which are up-regulated under shade treatment (32,33). Generally, gene expression fold-change in Kai Lan were either similar or higher than Choy Sum, which may explain the more severe SAS seen in Kai Lan (FIG. 11e). In both leaf blades and petioles of Kai Lan, the marker genes were highly up-regulated after short durations of shade treatment but gradually decreased over time (FIG. 11e). However, their expression patterns were slightly different in Choy Sum. For instance, the expression of XTH33 homologue was down-regulated in Choy Sum leaf blades under shade and PIL1 homologue was not detectable in Choy Sum petioles regardless of the shade duration (FIG. 11e). Moreover, while the expression of PAR1 homologue in Kai Lan returns to the baseline over time, the PAR1 homologues of Choy Sum (especially petioles) remains induced after prolonged shade treatment. In *Arabidopsis*, PAR1 inhibits phytochrome interacting factors (PIFs) from reducing carotenoids biosynthesis in shaded conditions (25). Therefore, the prolonged induction of PAR1 homologue in Choy Sum may explain the smaller decrease in carotenoids level during SAS. These results may correlate the differences in SAS response and respective carotenoids Raman peaks between Kai Lan and Choy Sum petioles.

Example 7

Early Diagnosis of SAS in Leafy Vegetables Using Raman Spectroscopy

Figure 14:
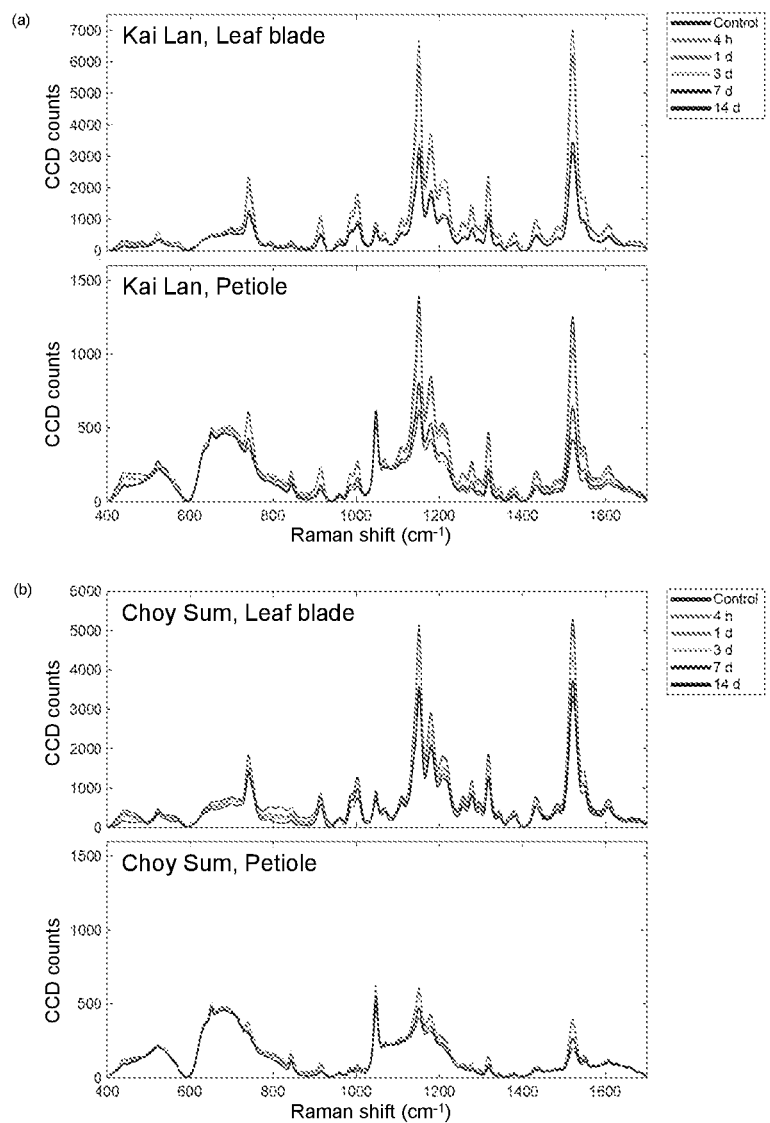
FIG. 14a-14b show Raman spectra of leafy vegetables with different duration of shade treatment.
Figure 15:
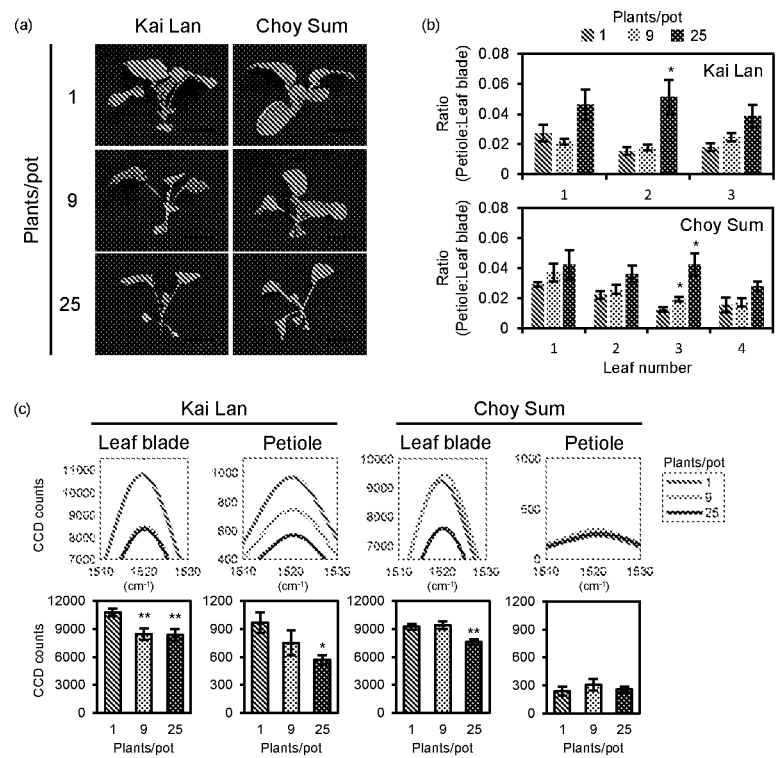
FIGS. 15a-15c show Raman spectra analysis of leafy vegetables at high density planting.

As shown, Raman spectroscopy was able to detect SAS in leafy vegetables like Kai Lan and Choy Sum. It was then investigated if Raman peaks of carotenoids could also be also used in the early diagnosis of SAS in leafy vegetables as it was applicable in *Arabidopsis*. Both vegetables were subjected to a 14 d time-course experiment under DS condition, similar to the time-course shade experiment performed with *Arabidopsis* plants (FIG. 5a). Both Kai Lan and Choy Sum displayed increasing SAS responses as the duration of shade treatment increased (FIG. 13a). Morphological changes in both Kai Lan and Choy Sum started after 3 d of shade treatment, as petioles of Kai Lan were elongated and leaf blades of both vegetables were reduced in size (FIG. 13b). Raman spectra of Kai Lan and Choy Sum in the time-course shade treatment showed that carotenoids peak reduced in all samples during SAS except Choy Sum petioles (FIG. 13c), which is consistent with the findings in FIG. 11c. After 14 d of shade, the carotenoids peak of Kai Lan leaf blades and petioles decreased by 50% and 49% respectively, while Choy Sum leaf blades showed a 29% decrease at 14 d shade and Choy Sum petioles displayed no significant changes (FIGS. 13c, 14a, 14b). Carotenoids peak intensity decreased within 1 to 3 d of shade treatment in Kai Lan and Choy Sum (FIGS. 13c, 14a, 14b). This decrease preceded clear morphological changes of leafy vegetables under shade condition (FIG. 13b). Therefore, these results show the relative shade tolerance in Choy Sum and demonstrated that the decrease in carotenoids Raman peaks can be used in early identification of SAS in *Brassica* vegetables.

Example 8

Raman Spectra Analysis of Leafy Vegetables Grown at High Density

Figure 16:
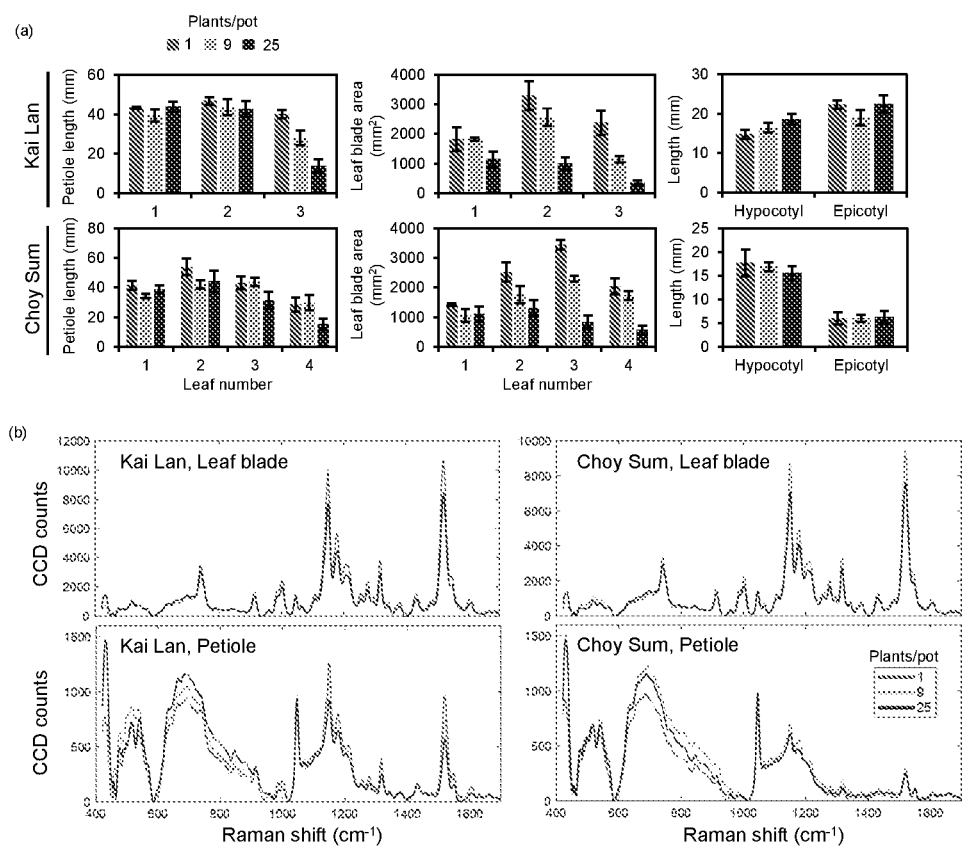
FIGS. 16a-16b show Raman spectra of leafy vegetables in high density planting.

Next, Raman spectra analysis was performed in Kai Lan and Choy Sum grown at low to high planting densities. At high density, both Kai Lan and Choy Sum developed SAS that were similar to those under shade conditions (FIGS. 15a, 15b, 16a). FIGS. 15c and 16b show that the carotenoids Raman peak also followed a similar trend to those observed in the shade conditions (FIG. 11c), thereby showing that this finding is likewise applicable in high-density growing of non-*Arabidopsis* plants Example 9

Detection of SAS Across Various Plant Species Using Raman Spectroscopy

Figure 18:
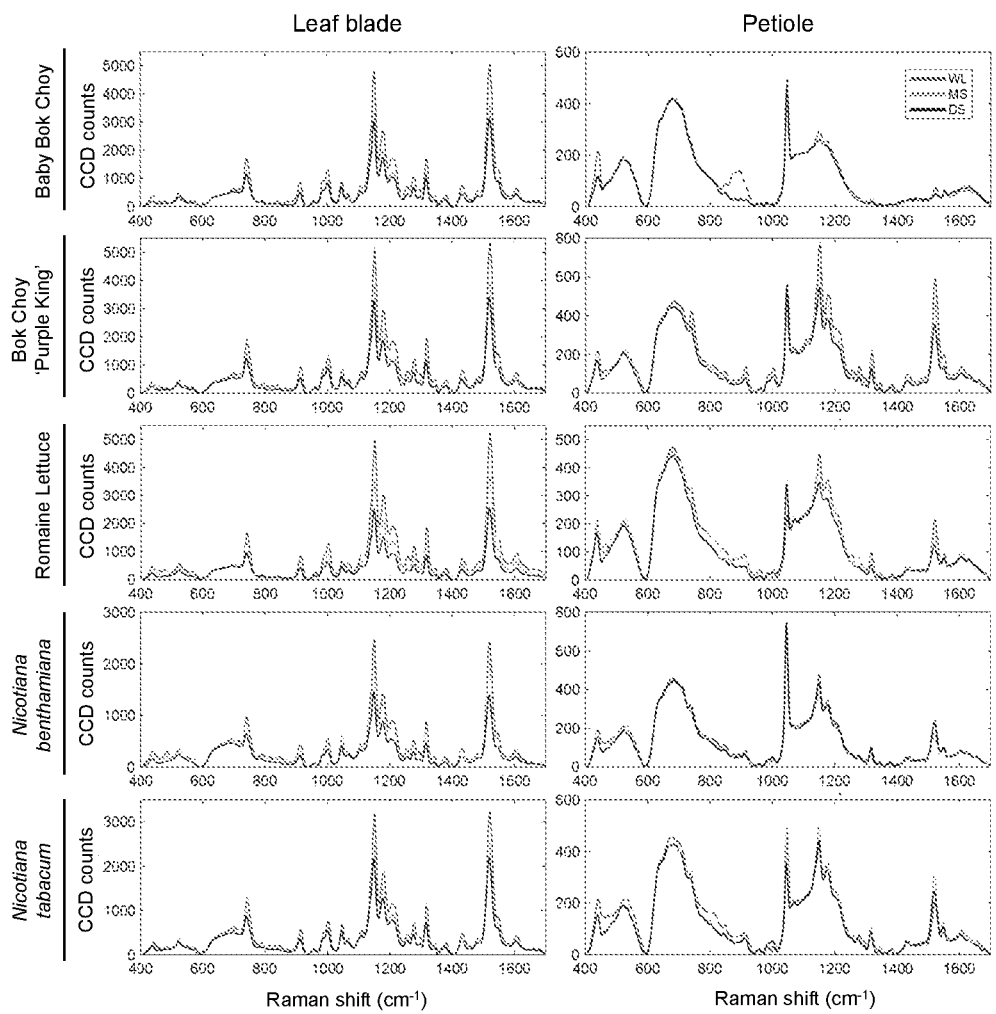
FIG. 18 shows Raman spectra of various plant species under shade conditions. Baby Bok Choy: leaf blade n=7, petiole n=4; Bok Choy 'Purple King': leaf blade n=6, petiole n=6; Romaine Lettuce: leaf blade n=6, petiole n=6; *Nicotiana benthamiana*: leaf blade n=3, petiole n=3; *Nicotiana tabacum*: leaf blade n=6, petiole n=3. WL, white light; MS, moderate shade; DS, deep shade

To demonstrate the general utility of Raman spectroscopy for the early diagnosis of SAS in plants, other types of vegetables and plants were tested, including Bok Choy cultivars (*Brassica rapa* var. *chinensis*), Romaine Lettuce (*Lactuca sativa* L. var. *longifolia*), and two tobacco species, *Nicotiana benthamiana* and *Nicotiana tabacum*. FIG. 17a shows that all tested plants displayed different degrees of SAS when subjected to shade treatment. Baby Bok Choy, Bok Choy 'Purple King', and Romaine lettuce were more sensitive to shade compared to the two tobacco species (FIG. 17a). This was detected by Raman spectroscopy, as the carotenoids peak intensities decreased in both leaf blades and petioles of two Bok Choy cultivars and Romaine lettuce in MS and DS (FIG. 17b, FIG. 18. Plants of *N. benthamiana* showed clear SAS only in DS, while *N. tabacum* did not show any elongation of petioles under shade (FIG. 17a). These greater tolerances to shade can be seen in the smaller decrease in the carotenoids peak intensities of leaf blades under shade and no changes in the petiole carotenoids peak (FIG. 17b, FIG. 18).

Overall, these results demonstrate that Raman peaks for carotenoids are widely applicable as an indicator of SAS regardless of the plant species, and that the changes in the peak intensity correlates well with the morphological changes in response to shade.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY (1) Franklin K. A. & Whitelam G. C. Phytochromes and shade-avoidance responses in plants. *Ann Bot.* 96, 169-175 (2005).

(2) Ballaré C. L. & Pierik R. The shade-avoidance syndrome: multiple signals and ecological consequences. *Plant Cell Environ.* 40, 2530-2543 (2017).

(3) Wille W., Pipper C. B., Rosenqvist E., Andersen S. B., & Weiner J. Reducing shade avoidance responses in a cereal crop. *AoB Plants* 9, plx039 (2017).

(4) Tang Y. & Liesche J. The molecular mechanism of shade avoidance in crops—How data from *Arabidopsis* can help to identify targets for increasing yield and biomass production. *J. Integr. Agric.* 16, 1244-1255 (2017).

(5) Casal J. J. Shade avoidance. *Arabidopsis Book.* 10, e0157 (2012).

(6) Rolauffs S., Fackendahl P., Sahm J., Fiene G. & Hoecker U. *Arabidopsis* COP1 and SPA genes are essential for plant elongation but not for acceleration of flowering time in response to a low red light to far-red light ratio. *Plant Physiol.* 160, 2015-2027 (2012).

(7) Devlin P. F., Yanovsky M. J. & Kay S. A. A genomic analysis of the shade avoidance response in *Arabidopsis*. *Plant Physiol.* 133, 1617-1629 (2003).

(8) Yang C. & Li L. Hormonal Regulation in Shade Avoidance. Front *Plant Sci.* 8, 1527 (2017).

(9) Chaiwanon J., Wang W., Zhu J. Y., Oh E. & Wang Z. Y. Information Integration and Communication in Plant Growth Regulation. *Cell.* 164, 1257-1268 (2016).

(10) Caldana C., Degenkolbe T., Cuadros-Inostroza A., Klie S., Sulpice R., Leisse A., Steinhauser D., Fernie A. R., Willmitzer L. & Hannah M. A. High-density kinetic analysis of the metabolomic and transcriptomic response of *Arabidopsis* to eight environmental conditions. *Plant J.* 67, 869-884 (2011).

(11) Jankanpaa H. J., Mishra Y., Schroder W. P. & Jansson S. Metabolic profiling reveals metabolic shifts in *Arabidopsis* plants grown under different light conditions. *Plant Cell Environ.* 35, 1824-1836 (2012).

(12) Ren J., Zhang A., Kong L., & Wang X. Advances in mass spectrometry-based metabolomics for investigation of metabolites. *RSC Adv.* 40, 22335-22350 (2018).

(13) Kumar R., Bohra A., Pandey A. K., Pandey M. K., & Kumar A. Metabolomics for Plant Improvement: Status and Prospects. Front. *Plant Sci.* 8, 1302 (2017).

(14) Jones W. P. & Kinghorn A. D. Extraction of Plant Secondary Metabolites. In *Natural Products Isolation*. (eds. Sarker S. & Nahar L.) Methods in Molecular Biology (Methods and Protocols), 864, 341-366 (Humana Press, 2012).

(15) Shalabaeva V., Lovato L., La Rocca R., Messina G. C., Dipalo M., Miele E., Perrone M., Gentile F. & De Angelis F. Time resolved and label free monitoring of extracellular metabolites by surface enhanced Raman spectroscopy. *PLoS One* 12, e0175581 (2017).

(16) Ding J., Xu T., Tan X., Jin H., Shao J., & Li H. Raman spectrum: A potential biomarker for embryo assessment during in vitro fertilization. *Exp Ther Med.* 13, 1789-1792 (2017).

(17) Chen N., Rong M., Shao X., Zhang H., Liu S., Dong B., Xue W., Wang T., Li T. & Pan J. Surface-enhanced Raman spectroscopy of serum accurately detects prostate cancer in patients with prostate-specific antigen levels of 4-10 ng/mL. *Int J Nanomedicine.* 12, 5399-5407 (2017).

(18) Premasiri W. R., Sauer-Budge A. F., Lee J. C., Klapperich C. M. & Ziegler L. D. Rapid bacterial diagnostics via surface enhanced Raman microscopy. *Spectroscopy (Springf).* 27, s8-s31 (2012).

(19) Ember K. J. I., Hoeve M. A., McAughtrie S. L., Bergholt M. S., Dwyer B. J., Stevens M. M., Faulds K., Forbes S. J. & Campbell C. J. Raman spectroscopy and regenerative medicine: a review. *NPJ Regen Med.* 2, 12 (2017).

(20) Raman C. V. & Krishnan K. S. A new type of secondary radiation. *Nature* 121, 501-502 (1928).

(21) Altangerel, N., Ariunbold, G. O., Gorman, C., Alkahtani, M. H., Borrego, E. J., Bohlmeyer, D., Hemmer, P., Kolomiets, M. V., Yuan, J. S. & Scully M. O. In vivo diagnostics of early abiotic plant stress response via Raman spectroscopy. *Proc. Natl. Acad. Sci. U.S.A* 114, 3393-3396 (2017).

(22) Leivar P., Monte E., Cohn M. M. & Quail P. H. Phytochrome signaling in green *Arabidopsis* seedlings: impact assessment of a mutually negative phyB-PIF feedback loop. *Mol. Plant.* 5, 734-749 (2012).

(23) Schwartz C. J., Lee J. & Amasino R. Variation in shade-induced flowering in *Arabidopsis thaliana* results from FLOWERING LOCUS T allelic variation. *PLoS One* 12, e0187768 (2017).

(24) Merzlyak M. N., Chivkunova O. B., Melo T. B. & Naqvi K. R. Does a leaf absorb radiation in the near infrared (780-900 nm) region? A new approach to quantifying optical reflection, absorption and transmission of leaves. *Photosyn. Res.* 72: 263-270 (2002).

(25) Bou-Torrent J., Toledo-Ortiz G., Ortiz-Alcaide M., Cifuentes-Esquivel N., Halliday K. J., Martinez-Garcia J. F. & Rodriguez-Concepcion M. Regulation of Carotenoid Biosynthesis by Shade Relies on Specific Subsets of Antagonistic Transcription Factors and Cofactors. *Plant Physiol.* 169, 1584-1594 (2015).

(26) Ruiz-Sola M. A. & Rodriguez-Concepción M. Carotenoid biosynthesis in *Arabidopsis*: a colorful pathway. *Arabidopsis Book.* 10, e0158 (2012).

(27) Franklin K. A. & Quail P. H. Phytochrome functions in *Arabidopsis* development. *J. Exp. Bot.* 61, 11-24 (2010).

(28) Yang C., Xie F., Jiang Y., Li Z., Huang X. & Li L. Phytochrome A Negatively Regulates the Shade Avoidance Response by Increasing Auxin/Indole Acidic Acid Protein Stability. *Dev Cell.* 44, 29-41. e4 (2018).

(29) Yoshida Y., Sarmiento-Mañus R., Yamori W., Ponce M. R., Micol J. L. & Tsukaya H. The *Arabidopsis* phyB-9 Mutant Has a Second-Site Mutation in the VENOSA4 Gene That Alters Chloroplast Size, Photosynthetic Traits, and Leaf Growth. *Plant Physiol.* 178, 3-6 (2018).

(30) Reed J. W., Nagpal P., Poole D. S., Furuya M. & Chory J. Mutations in the gene for the red/far-red light receptor phytochrome B alter cell elongation and physiological responses throughout *Arabidopsis* development. *Plant Cell.* 5, 147-157 (1993).

(31) Guo D., Song X., Yuan M., Wang Z., Ge W., Wang L., Wang J. & Wang X. RNA-Seq Profiling Shows Divergent Gene Expression Patterns in *Arabidopsis* Grown under Different Densities. Front. *Plant Sci.* 8, 2001 (2017).

(32) Ma L. & Li G. Auxin-Dependent Cell Elongation During the Shade Avoidance Response. Front *Plant Sci.* 10, 914 (2019).

(33) Procko C., Crenshaw C. M., Ljung K., Noel J. P., Chory J. Cotyledon-Generated Auxin Is Required for Shade-Induced Hypocotyl Growth in *Brassica rapa. Plant Physiol.* 165, 1285-1301 (2014).

(34) Altangerel N., Ariunbold G. O., Gorman C., Alkahtani M. H., Borrego E. J., Bohlmeyer D., Hemmer P., Kolomiets M. V., Yuan J. S. & Scully M. O. Reply to Dong and Zhao: Plant stress via Raman spectroscopy. *Proc. Natl. Acad. Sci. U.S.A* 114, E5488-E5490 (2017).

(35) Dunn J. L., Turnbull J. D., & Robinson S. A. Comparison of solvent regimes for the extraction of photosynthetic pigments from leaves of higher plants. *Funct. Plant Biol.* 31, 195-202 (2004).

(36) Reed J. W., Nagatani A., Elich T. D., Fagan M. & Chory J. Phytochrome A and Phytochrome B Have Overlapping but Distinct Functions in *Arabidopsis* Development. *Plant Physiol.* 104, 1139-1149 (1994).

(37) Schneider C. A., Rasband W. S. & Eliceiri K. W. NIH Image to ImageJ: 25 years of image analysis. *Nature methods* 9, 671-675 (2012).

(38) Schindelin J., Arganda-Carreras I., Frise E., Kaynig V., Longair M., Pietzsch T., Preibisch S., Rueden C., Saalfeld S., Schmid B., Tinevez J. Y., White D. J., Hartenstein V., Eliceiri K., Tomancak P. & Cardona A. Fiji: an open-source platform for biological-image analysis. *Nature methods* 9, 676-682 (2012).

(39) Maloof J. N., Nozue K., Mumbach M. R. & Palmer C. M. LeafJ: an ImageJ plugin for semi-automated leaf shape measurement. *J Vis. Exp.* 71, 50028 (2013).

(40) Lieber C A., & Mahadevan-Jansen A. Automated method for subtraction of fluorescence from biological Raman spectra. *Appl Spectrosc.* 57, 1363-1367 (2003).

(41) Creely C. M., Singh G. P. & Petrov D. Dual wavelength optical tweezers for confocal Raman spectroscopy. *Opt Commun.* 245, 465-470 (2005).

(42) Huala E., Dickerman A. W., Garcia-Hernandez M., Weems D., Reiser L., LaFond F., Hanley D., Kiphart D., Zhuang M., Huang W., Mueller L. A., Bhattacharyya D., Bhaya D., Sobral B. W., Beavis W., Meinke D. W., Town C. D., Somerville C. & Rhee S. Y. The *Arabidopsis* Information Resource (TAIR): a comprehensive database and web-based information retrieval, analysis, and visualization system for a model plant. *Nucleic Acids Res.,* 29, 102-105, (2001).

(43) Goodstein D. M., Shu S., Howson R., Neupane R., Hayes R. D., Fazo J., Mitros T., Dirks W., Hellsten U., Putnam N. & Rokhsar D. S. Phytozome: a comparative platform for green plant genomics. *Nucleic Acids Res.* 40 (Database issue), D1178-D1186 (2012).

(44) Wellburn A. R. & Lichtenthaler H. Formulae and Program to Determine Total Carotenoids and Chlorophylls A and B of Leaf Extracts in Different Solvents. In *Advances in Photosynthesis Research* (ed. Sybesma C.). Advances in Agricultural Biotechnology, 2 (Springer, 1984).

(45) McDougall R, Kristiansen P, Rader R. Small-scale urban agriculture results in high yields but requires judicious management of inputs to achieve sustainability. *PNAS* 116, 129-134 (2019).

(46) Beacham A M, Vickers L, Monaghan J. Vertical farming: a summary of approaches to growing skywards. *J Hortic Sci Biotech* 94, 1-7 (2019).

What is claimed:

1. A method of diagnosing Shade Avoidance Syndrome (SAS) in a plant comprising:
   obtaining a Raman spectra of carotenoids in vivo and in situ in tissue of a plant leaf at a first point in time, wherein the Raman spectra includes one or more peaks characteristic of carotenoids;
   obtaining a Raman spectra of carotenoids in vivo and in situ in the tissue of the plant leaf at a second point in time, wherein the Raman spectra includes the one or more peaks characteristic of carotenoids;
   comparing intensity of the one or more peaks characteristic of carotenoids from the Raman spectra obtained at the first point of time with intensity of the one or more peaks characteristic of carotenoids from the Raman spectra obtained at the second point of time; and
   determining if there is a decrease in the relative intensity of the one or more peaks characteristic of carotenoids from the Raman spectra obtained at the second point in time,
   wherein a decrease in relative intensity of one or more peaks characteristic of carotenoids from the Raman spectra obtained at the second point of time is indicative of SAS.

2. The method of claim 1, wherein the tissue of the plant leaf is a leaf blade or a leaf petiole.

3. The method of claim 1, wherein the tissue of the plant leaf is the leaf blade.

4. The method of claim 1, wherein the one or more peaks characteristic of carotenoids in the Raman spectra are selected from the group of peaks consisting of 1004 $cm^{-1}$, 1150 $cm^{-1}$ and 1521 $cm^{-1}$.

5. The method of claim 1, wherein the Raman spectra is obtained using near-infrared excitation wavelength.

6. The method of claim 5, wherein the near-infrared excitation wavelength is 830 nm.

7. The method of claim 1, wherein obtaining the Raman spectra is non-invasive and non-destructive to the tissue of the plant leaf.

8. A method of preventing or slowing the further development of Shade Avoidance Syndrome (SAS) in a plant comprising:
   diagnosing SAS in a plant according to the method of claim 1;
   and reducing the amount of shade affecting the plant.

9. The method of claim 8, wherein shade is reduced by providing light to the plant.

10. The method of claim 8, wherein shade is reduced by trimming nearby plants.

* * * * *

SEQUENCE LISTING

<160> NUMBER OF SEQ ID NOS: 40

<210> SEQ ID NO 1
<211> LENGTH: 20
<212> TYPE: DNA
<213> ORGANISM: Arabidopsis thaliana

<400> SEQUENCE: 1
catgagccca cccactactt                                              20

<210> SEQ ID NO 2
<211> LENGTH: 20
<212> TYPE: DNA
<213> ORGANISM: Arabidopsis thaliana

<400> SEQUENCE: 2
acctaggacg aagagcgtca                                              20

<210> SEQ ID NO 3
<211> LENGTH: 20
<212> TYPE: DNA
<213> ORGANISM: Arabidopsis thaliana

<400> SEQUENCE: 3
gaacgtgtct cctcctctgc                                              20

<210> SEQ ID NO 4
<211> LENGTH: 20
<212> TYPE: DNA
<213> ORGANISM: Arabidopsis thaliana

<400> SEQUENCE: 4
cctagcgacc tgattttgc                                               20

<210> SEQ ID NO 5
<211> LENGTH: 21
<212> TYPE: DNA
<213> ORGANISM: Arabidopsis thaliana

<400> SEQUENCE: 5
cagcaacacc aacatcaata c                                            21

<210> SEQ ID NO 6
<211> LENGTH: 21
<212> TYPE: DNA
<213> ORGANISM: Arabidopsis thaliana

<400> SEQUENCE: 6
tggaattagt ccacttgggt g                                            21

<210> SEQ ID NO 7
<211> LENGTH: 20
<212> TYPE: DNA
<213> ORGANISM: Arabidopsis thaliana

<400> SEQUENCE: 7
ctagcaaccc tcacctccga                                              20

<210> SEQ ID NO 8
<211> LENGTH: 26
<212> TYPE: DNA
<213> ORGANISM: Arabidopsis thaliana

<400> SEQUENCE: 8
tcgtaacaca caatctcatt gccaaa                                          26

<210> SEQ ID NO 9
<211> LENGTH: 20
<212> TYPE: DNA
<213> ORGANISM: Arabidopsis thaliana

<400> SEQUENCE: 9
tcgcaaaggg tatgacaaag                                                 20

<210> SEQ ID NO 10
<211> LENGTH: 19
<212> TYPE: DNA
<213> ORGANISM: Arabidopsis thaliana

<400> SEQUENCE: 10
cagtcccgct tatcattcc                                                  19

<210> SEQ ID NO 11
<211> LENGTH: 20
<212> TYPE: DNA
<213> ORGANISM: Arabidopsis thaliana

<400> SEQUENCE: 11
ttgggttggc ctgatatgcg                                                 20

<210> SEQ ID NO 12
<211> LENGTH: 20
<212> TYPE: DNA
<213> ORGANISM: Arabidopsis thaliana

<400> SEQUENCE: 12
agtcattgtg cctccagctc                                                 20

<210> SEQ ID NO 13
<211> LENGTH: 20
<212> TYPE: DNA
<213> ORGANISM: Arabidopsis thaliana

<400> SEQUENCE: 13
ttcgaagggt ttcgatcccg                                                 20

<210> SEQ ID NO 14
<211> LENGTH: 20
<212> TYPE: DNA
<213> ORGANISM: Arabidopsis thaliana

<400> SEQUENCE: 14
ttgcgtcttg tcgctcttga                                                 20

<210> SEQ ID NO 15
<211> LENGTH: 20
<212> TYPE: DNA
<213> ORGANISM: Arabidopsis thaliana

<400> SEQUENCE: 15
gacacccgaa aggcgaaagg                                                 20

<210> SEQ ID NO 16
<211> LENGTH: 20
<212> TYPE: DNA
<213> ORGANISM: Arabidopsis thaliana

```
<400> SEQUENCE: 16
cagcgagagc agcatcaagc                                              20

<210> SEQ ID NO 17
<211> LENGTH: 20
<212> TYPE: DNA
<213> ORGANISM: Arabidopsis thaliana

<400> SEQUENCE: 17
gtcggtcacg cgctcaggta                                              20

<210> SEQ ID NO 18
<211> LENGTH: 21
<212> TYPE: DNA
<213> ORGANISM: Arabidopsis thaliana

<400> SEQUENCE: 18
cgagatgctg acatggccag a                                            21

<210> SEQ ID NO 19
<211> LENGTH: 19
<212> TYPE: DNA
<213> ORGANISM: Arabidopsis thaliana

<400> SEQUENCE: 19
gcagattttc gttaaaacc                                               19

<210> SEQ ID NO 20
<211> LENGTH: 17
<212> TYPE: DNA
<213> ORGANISM: Arabidopsis thaliana

<400> SEQUENCE: 20
ccaaagttct gccgtcc                                                 17

<210> SEQ ID NO 21
<211> LENGTH: 20
<212> TYPE: DNA
<213> ORGANISM: Brassica oleracea

<400> SEQUENCE: 21
tatcattgct ggacgaggcg                                              20

<210> SEQ ID NO 22
<211> LENGTH: 20
<212> TYPE: DNA
<213> ORGANISM: Brassica oleracea

<400> SEQUENCE: 22
ctgcgcccat atgcattcct                                              20

<210> SEQ ID NO 23
<211> LENGTH: 20
<212> TYPE: DNA
<213> ORGANISM: Brassica oleracea

<400> SEQUENCE: 23
ggtggtttcg aacgcagaac                                              20

<210> SEQ ID NO 24
<211> LENGTH: 20
<212> TYPE: DNA
<213> ORGANISM: Brassica oleracea
```

```
<400> SEQUENCE: 24
ttcttcttgg ccggagacac                                              20

<210> SEQ ID NO 25
<211> LENGTH: 21
<212> TYPE: DNA
<213> ORGANISM: Brassica oleracea

<400> SEQUENCE: 25
ggacttagac cgtcatcgtc a                                            21

<210> SEQ ID NO 26
<211> LENGTH: 20
<212> TYPE: DNA
<213> ORGANISM: Brassica oleracea

<400> SEQUENCE: 26
ggtaatagcc agtcgccctc                                              20

<210> SEQ ID NO 27
<211> LENGTH: 20
<212> TYPE: DNA
<213> ORGANISM: Brassica oleracea

<400> SEQUENCE: 27
tcgccaaact cactctcgac                                              20

<210> SEQ ID NO 28
<211> LENGTH: 20
<212> TYPE: DNA
<213> ORGANISM: Brassica oleracea

<400> SEQUENCE: 28
accacaacac cagaggcaaa                                              20

<210> SEQ ID NO 29
<211> LENGTH: 20
<212> TYPE: DNA
<213> ORGANISM: Brassica oleracea

<400> SEQUENCE: 29
catgttcacc acaacagccg                                              20

<210> SEQ ID NO 30
<211> LENGTH: 20
<212> TYPE: DNA
<213> ORGANISM: Brassica oleracea

<400> SEQUENCE: 30
agtctccatc tcctgctcgt                                              20

<210> SEQ ID NO 31
<211> LENGTH: 20
<212> TYPE: DNA
<213> ORGANISM: Brassica rapa

<400> SEQUENCE: 31
ggttttcccc ggatcaacga                                              20

<210> SEQ ID NO 32
<211> LENGTH: 20
<212> TYPE: DNA
```

<213> ORGANISM: Brassica rapa

<400> SEQUENCE: 32
cacgaaggca cgacgaattg                                                   20

<210> SEQ ID NO 33
<211> LENGTH: 20
<212> TYPE: DNA
<213> ORGANISM: Brassica rapa

<400> SEQUENCE: 33
tttgagcgca gaaccaaacg                                                   20

<210> SEQ ID NO 34
<211> LENGTH: 20
<212> TYPE: DNA
<213> ORGANISM: Brassica rapa

<400> SEQUENCE: 34
aatcctctgc aacgcctcaa                                                   20

<210> SEQ ID NO 35
<211> LENGTH: 21
<212> TYPE: DNA
<213> ORGANISM: Brassica rapa

<400> SEQUENCE: 35
ggacttagac cgtcatcgtc a                                                 21

<210> SEQ ID NO 36
<211> LENGTH: 20
<212> TYPE: DNA
<213> ORGANISM: Brassica rapa

<400> SEQUENCE: 36
ggtaatagcc agtcgccctc                                                   20

<210> SEQ ID NO 37
<211> LENGTH: 20
<212> TYPE: DNA
<213> ORGANISM: Brassica rapa

<400> SEQUENCE: 37
tttgcctctg gtgttgtggt                                                   20

<210> SEQ ID NO 38
<211> LENGTH: 25
<212> TYPE: DNA
<213> ORGANISM: Brassica rapa

<400> SEQUENCE: 38
actctatgtc tatctcatcg tgggt                                             25

<210> SEQ ID NO 39
<211> LENGTH: 20
<212> TYPE: DNA
<213> ORGANISM: Brassica rapa

<400> SEQUENCE: 39
catgttcacc acaacagccg                                                   20

<210> SEQ ID NO 40
<211> LENGTH: 20

```
<212> TYPE: DNA
<213> ORGANISM: Brassica rapa

<400> SEQUENCE: 40
agtctccatc tcctgctcgt                                              20
```